United States Patent
Loukas et al.

(10) Patent No.: US 9,637,527 B2
(45) Date of Patent: May 2, 2017

(54) METHOD FOR TREATING INFLAMMATION WITH AN AC-TMP-2 PROTEIN

(71) Applicant: JAMES COOK UNIVERSITY, Townsville, Queensland (AU)

(72) Inventors: Alex Loukas, Smithfield (AU); Severine Navarro, Smithfield (AU)

(73) Assignee: JAMES COOK UNIVERSITY, Townsville (AU)

( * ) Notice: Subject to any disclaimer, the term of this patent is extended or adjusted under 35 U.S.C. 154(b) by 70 days.

(21) Appl. No.: 14/384,681

(22) PCT Filed: Mar. 13, 2013

(86) PCT No.: PCT/AU2013/000247
§ 371 (c)(1),
(2) Date: Sep. 11, 2014

(87) PCT Pub. No.: WO2013/134822
PCT Pub. Date: Sep. 19, 2013

(65) Prior Publication Data
US 2015/0037366 A1    Feb. 5, 2015

(30) Foreign Application Priority Data

Mar. 13, 2012 (AU) ................................ 2012900999

(51) Int. Cl.
| C07K 14/435 | (2006.01) |
| A61K 38/57 | (2006.01) |
| A61K 39/00 | (2006.01) |
| A61K 45/06 | (2006.01) |

(52) U.S. Cl.
CPC .......... *C07K 14/4354* (2013.01); *A61K 38/57* (2013.01); *A61K 39/0003* (2013.01); *A61K 45/06* (2013.01)

(58) Field of Classification Search
None
See application file for complete search history.

(56) References Cited

U.S. PATENT DOCUMENTS

2005/0042232 A1    2/2005    Hotez et al.

FOREIGN PATENT DOCUMENTS

| WO | WO 93/23063 | 11/1993 |
| WO | WO 2006/019962 | 2/2006 |
| WO | WO 2010/048432 | 4/2010 |

OTHER PUBLICATIONS

Ruyssers et al., Therapeutic potential of helminth soluble proteins in TNBS induced colitis in mice, Inflamm. Bowel Dis. 15, 491-500, 2009.*
Kumagai et al., The involvement of matrix metalloproteinases in basement membrane injury in murine model of acute allergic airway inflammation, Clin. Exp. Allergy, 32, 1527-1534, 2002.*
Miyoshi et al., Beneficial effects of tissue inhibitor of metalloproteinases-2 (TIMP-2) on chronic dermatitis, J. Dermatol., 32, 346-353, 2005.*
van Assche G., Emerging drugs to treat Crohn's disease, Exp. Op. Emerg. Drugs, 12, 49-59, 2007.*
Cuellar et al., "The Hookworm Tissue Inhibitor of Metalloproteases (Ac-TMP-1) Modifies Dendritic Cell Function and Induces Generation of CD4 and CD8 Suppressor T Cells", PLoS Negl Trop Dis 3(5):e439. doi.:10.1371/journal.pntd.0000439 (9 pages).
Zhan et al., "Molecular cloning and Characterization of Ac-TMP-2, a tissue inhibitor of metalloproteinase secreted by adult *Ancylostoma caninum*", Mol Biochem Parasi. 162:142-148, 2008.
International Search Report (ISR) for PCT/AU2013/000247, mailed Apr. 23, 2013 (3 pages).
International Preliminary Report on Patentability (IPRP) with amended sheets, mailed Sep. 26, 2013 (10 pages).
Butler et al., "The Specificity of TIMP-2 for Matrix Metalloproteinases Can Be Modified by Single Amino Acid Mutations," J. Biol. Chem. vol. 274, No. 29, pp. 20391-20396, 1999.
Mulvenna et al., "Proteomics Analysis of the Excretory/Secretory Component of the Blood-feeding Stage of the Hookworm, *Ancylostoma caninum*," Mol. Cell. Proteomics, vol. 8.1, pp. 109-121, 2009.

* cited by examiner

Primary Examiner — Elly-Gerald Stoica
(74) Attorney, Agent, or Firm — Klarquist Sparkman

(57) ABSTRACT

A method for reducing or alleviating inflammation in a subject includes administering to the subject a therapeutically effective amount of: (a) Ac-TMP-1 or a biologically active fragment or variant of Ac-TMP-1; (b) Ac-TMP-2 or a biologically active fragment or variant of Ac-TMP-2; or (c) a combination of (a) and (b), to thereby reduce or alleviate inflammation in the subject. A method for preventing or treating asthma or inflammatory bowel disease in a subject includes administering to the subject a therapeutically effective amount of: (a) Ac-TMP-1 or a biologically active fragment or variant of Ac-TMP-1; (b) Ac-TMP-2 or a biologically active fragment or variant of Ac-TMP-2; or (c) a combination of (a) and (b), to thereby prevent or treat asthma or inflammatory bowel disease in the subject. The subject may be a mammal, inclusive of humans.

22 Claims, 12 Drawing Sheets

```
1           M  R  V  A  I  V  F  I  A  C  F  A  V  A  H  A  C
1   AGCATATCAGCATGAGAGTCGCTATTGTTTTCATTGCATGCTTCGCAGTAGCACACGCAT
18    K  C  E  K  K  P  R  P  P  L  E  K  L  L  C  Q  S  Q  F  V
61  GCAAGTGCGAAAAGAAACCTCGTCCTCCATTGGAGAAACTGCTTTGCCAATCACAATTTG
38    T  H  A  K  V  T  K  K  R  I  D  G  Y  F  I  Y  Y  D  L  E
121 TTACTCACGCGAAAGTGACGAAGAAGAGAATTGATGGTTACTTCATCTATTACGACTTGG
58    H  K  E  V  Y  K  P  K  D  R  S  I  P  I  E  L  F  S  W  R
181 AGCATAAGGAAGTTTATAAGCCCAAAGATAGGAGTATCCCAATCGAACTCTTCTCATGGA
48    E  K  E  N  C  G  V  P  D  L  E  E  G  K  E  Y  L  I  G  G
241 GGGAAAAGGAAAATTGTGGTGTTCCGGATCTCGAAGAAGGCAAAGAATACCTGATAGGAG
98    K  V  T  D  Y  G  D  G  D  L  V  I  S  V  S  R  C  D  L  L
301 GTAAAGTGACGGATTATGGCGACGGTGATTTGGTAATTTCTGTTTCACGGTGCGACCTTC
118   R  N  W  T  D  V  S  G  E  E  K  K  L  L  G  T  F  K  C  E
361 TCCGAAACTGGACAGACGTCTCTGGAGAGGAGAAGAAATTGCTCGGAACGTTCAAATGTG
138   N  Q  S  *  (SEQ ID NO:1)
421 AAAATCAGTCATAAACGCCGATTATATATAATTGAAAGAAGAGAAATGAACATTTTTCAC

481 GCGAAAAAAAAAAAAAAAAAAAAAAAAAAAAAAAAAAAAAAA
```

Figure 1

```
1   CCTCGTGCCGAATGGCACGAGGGTTTGAGGTACAGAAGGGCGCCGAAGTTATACTAAACC
1     M  I  S  L  I  V  F  I  A  C  L  T  T  T  Q  A  A  C  S  C
61  CATGATTTCTCTCATAGTTTTCATTGCATGCCTCACAACGACGCAGGCAGCATGCTCTTG
21    K  P  F  G  T  L  K  E  A  F  C  Q  S  D  Y  V  L  L  A  K
121 CAAACCGTTCGGAACACTGAAGGAAGCTTTCTGCCAATCAGATTACGTGCTTCTGGCAAA
41    V  L  S  V  N  S  K  Y  G  E  S  S  R  N  E  A  N  D  M  S
181 AGTGTTGTCAGTAAATAGTAAATATGGTGAATCGTCGAGAAATGAAGCAAATGATATGAG
61    T  T  A  N  G  T  W  S  Y  H  V  W  H  M  R  T  W  K  G  P
241 CACGACCGCTAACGGAACATGGAGTTACCATGTATGGCACATGCGGACTTGGAAGGGTCC
81    V  V  D  T  S  V  L  T  T  S  Y  S  E  C  G  V  T  G  L  L
301 TGTCGTTGATACTAGTGTTCTCACCACGTCATATAGCGAGTGTGGTGTAACTGGTCTCTT
101   K  N  W  D  Y  F  L  T  G  K  Q  G  K  D  G  E  I  T  I  T
361 GAAAAATTGGGATTATTTTCTAACAGGCAAGCAAGGAAAAGATGGCGAAATCACCATCAC
121   S  C  D  F  V  M  P  S  T  D  V  T  P  E  E  H  D  L  L  M
421 AAGCTGCGACTTTGTAATGCCATCAACTGATGTCACACCAGAAGAGCATGATCTTTTGAT
141   D  L  M  G  D  P  K  K  C  E  E  K  D  D  E  R  D  V  K  E
481 GGACCTCATGGGGGACCCGAAAAAATGTGAAGAAAAAGATGATGAGAGGGACGTTAAAGA
161   N  E  N  S  V  E  E  N  D  E  K  D  E  E  E  N  G  E  K  T
541 AAACGAGAATAGCGTAGAAGAGAATGATGAGAAAGATGAAGAAGAAAATGGTGAGAAAAC
181   V  E  E  N  D  E  K  T  V  E  E  N  D  E  K  V  E  E  E  N
601 AGTAGAAGAGAATGACGAGAAAACTGTGGAAGAAAACGATGAGAAAGTTGAAGAAGAAAA
201   G  E  K  T  V  E  E  N  D  E  K  T  V  E  E  N  D  E  K  D
661 TGGTGAGAAAACAGTAGAAGAGAATGACGAGAAAACTGTGGAAGAAAACGATGAGAAAGA
221   E  E  N  G  E  K  T  V  E  E  N  D  E  K  T  V  E  E  N
721 TGAAGAAGAAAATGGTGAGAAAACAGTAGAGGAGAATGACGAGAAAACTGTGGAAGAAAA
241   D  E  Q  E  *  (SEQ ID NO:2)
781 CGATGAACAGGAGTGATCTGAACACTGCAATTTCTCGTAACCAAGTGGGAATAAAATTCT

841 GACGAAAAAAAAAAAAAAAAAAAAAAAAAAAA
```

Figure 2

METHOD FOR TREATING INFLAMMATION WITH AN *AC*-TMP-2 PROTEIN

CROSS REFERENCE TO RELATED APPLICATIONS

This is the U.S. National Stage of International Application No. PCT/AU2013/000247, filed Mar. 13, 2013, which was published in English under PCT Article 21(2), which in turn claims the benefit of Australia Application No. 2012900999, filed Mar. 13, 2012. The Australia application is incorporated herein in its entirety.

FIELD OF THE INVENTION

THIS INVENTION relates to methods for treating inflammation. More particularly, this invention relates to the use of hookworm excretory/secretory proteins for reducing, alleviating and/or preventing inflammation.

BACKGROUND TO THE INVENTION

Inflammation is a non-specific reaction mounted by the immune system in response to a perceived injury or threat. It is an innate defensive response, distinguished from the more precisely tailored adaptive responses of the immune system. Inflammation may work cooperatively with adaptive responses of the immune system, which develop more slowly but are more precisely targeted to a harmful agent such as a pathogen that may be causing localised injury.

While associated with infection, inflammation occurs in response to many types of injury, including physical trauma, burns (e.g., from radiation, heat or corrosive materials), chemical or particulate irritants, bacterial or viral pathogens, and localized oxygen deprivation (ischemic). Inflammation is also associated with autoimmune diseases and allergic reactions. Inflammation includes the classic symptoms of redness, heat, swelling, and pain, and may be accompanied by decreased function of the inflamed organ or tissue.

While a number of methods for treating inflammation are known, all of them have limitations, particularly with regard to broad based efficacy. Thus, there is a need for new methods for reducing, alleviating and/or preventing inflammation associated with a variety of causes.

SUMMARY OF THE INVENTION

The present invention is directed to methods and compositions for treating and/or preventing inflammation and/or diseases or conditions associated with inflammation.

In a broad form, the invention relates to use of one or more tissue metalloprotease inhibitor proteins derivable or obtainable from hookworms including but not limited to *Ancylostoma caninum*, for reducing, alleviating and/or preventing inflammation and/or diseases or conditions associated with inflammation such as asthma and/or inflammatory bowel disease.

In one aspect, the invention provides a method of reducing or alleviating inflammation in a subject, the method including the step of administering to the subject a therapeutically effective amount of: (a) Ac-TMP-1 (SEQ ID NO:1) or a biologically active fragment or variant of Ac-TMP-1, (b) Ac-TMP-2 (SEQ ID NO:2) or a biologically active fragment or variant of Ac-TMP-2, or (c) a combination of (a) and (b).

In one embodiment, this aspect further includes the step of administering to the subject at least one additional agent.

Suitably, according to the above embodiment, the at least one additional agent is selected from the group consisting of nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents), antibiotics, and combinations thereof.

In some embodiments, the inflammation is associated with or secondary to a disease, disorder and/or condition in the subject, particularly an immunological disease, disorder and/or condition.

In certain embodiments the disease is a disease of the digestive tract or the respiratory system.

In another embodiment, the disease, disorder and/or condition is refractory to a baseline therapy.

Suitably, according to the above embodiment, the baseline therapy comprises administration of at least one baseline agent selected from the group consisting of nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents), antibiotics, and combinations thereof.

In another aspect, the invention provides a method of preventing inflammation in a subject, the method including the step of administering to the subject a therapeutically effective amount of: (a) Ac-TMP-1 (SEQ ID NO:1) or a biologically active fragment or variant of Ac-TMP-1, (b) Ac-TMP-2 (SEQ ID NO:2) or a biologically active fragment or variant of Ac-TMP-2, or (c) a combination of (a) and (b).

In one embodiment, this aspect further includes the step of administering to the subject at least one additional agent.

In yet another aspect, the invention provides a method of treating and/or preventing an inflammatory bowel disease in a subject, the method including the step of administering to the subject a therapeutically effective amount of (a) Ac-TMP-1 (SEQ ID NO:1) or a biologically active fragment or variant of Ac-TMP-1, (b) Ac-TMP-2 (SEQ ID NO:2) or a biologically active fragment or variant of Ac-TMP-2, or (c) a combination of (a) and (b).

In one embodiment, this aspect further includes the step of administering to the subject at least one additional agent.

Suitably, according to the above embodiment, the at least one additional agent is selected from the group consisting of nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-GR agents), antibiotics, and combinations thereof.

In a further aspect, the invention provides a method of treating and/or preventing asthma in a subject, the method including the step of administering to the subject a therapeutically effective amount of: (a) Ac-TMP-1 (SEQ ID NO:1) or a biologically active fragment or variant of Ac-TMP-1, (b) Ac-TMP-2 (SEQ ID NO:2) or a biologically active fragment or variant of Ac-TMP-2, or (c) combination of (a) and (b).

In one embodiment, this aspect further includes the step of administering to the subject at least one additional agent.

Suitably, according to the above embodiment, the at least one additional agent is selected from the group consisting of nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents), antibiotics, and combinations thereof.

Preferably, the subject is a mammal.

More preferably, the subject is a human.

A yet further aspect of the invention provides a pharmaceutical composition comprising a therapeutically effective amount of: (a) Ac-TMP-1 (SEQ ID NO:1) or a biologically active fragment or variant of Ac-TMP-1, (b) Ac-TMP-2 (SEQ ID NO:2) or a biologically active fragment or variant of Ac-TMP-2, or (c) a combination of (a) and (b) together with a pharmaceutically acceptable carrier diluent of excipient.

In some embodiments, the pharmaceutical composition may further comprise at least one additional agent.

The at least one additional agent may be selected from the group consisting of nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents; and anti-IL-6R agents), antibiotics, and combinations thereof.

Suitably, the pharmaceutical composition is for preventing or treating inflammation and/or for preventing or treating a disease or condition associated with inflammation.

BRIEF DESCRIPTION OF THE FIGURES

FIG. 1. Nucleotide sequence and amino acid sequence (SEQ ID NO:1) of Ac-TMP-1 (Zhan et al., *Am. J. Trop. Med. Hyg.* 66:238-44, 2002).

FIG. 2. Nucleotide sequence and amino acid sequence (SEQ ID NO:2) of Ac-TMP-2 (Zhan et al., *Mol. Biochem. Parasitology* 162:142-48, 2008).

SEQUENCE LISTING

Figure 3:
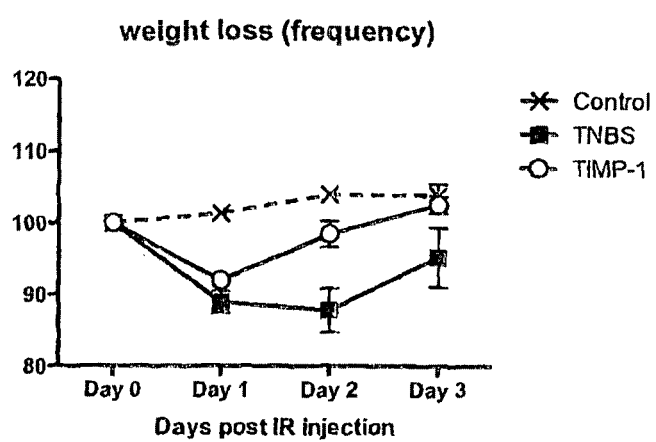
FIG. 3. Purified recombinant Ac-TMP-1 protects against TNBS-induced weight loss. Briefly, mice received on day 0 a single intraperitoneal injection with 20 μg of Ac-TMP-1 (TIMP), or a mock PBS injection (TNBS). Five hours later, they received an intrarectal injection with 2.5 mg of 2,4,6-trinitrobenzene sulfonic acid (commonly referred to as TNBS) in 45% ethanol, under a mild anaesthetic. From day 0 to day 3, mice were monitored daily for weight loss. The control group (Control) did not receive any injections and were not administered TNBS. Ac-TMP-1 significantly protected the mice from weight loss shown as a mean for each group of mice when compared to the TNBS group that received the mock injection.

The nucleic and amino acid sequences listed in the accompanying sequence listing are shown using standard letter abbreviations for nucledotide bases, and three letter code for amino acids, as defined in 37 C.F.R. 1.822. Only one strand of each nucleic acid sequence is shown, but the complementary starnd is understood as included by any reference to the displayed strand. The Sequence Listing is submitted as an ASCII text file named 93713-01_Seqs.txt, created on Sep. 11, 2014, ~8 KB, which is incorporated by reference herein.

DETAILED DESCRIPTION OF THE INVENTION

The present invention relates to methods for reducing, alleviating and/or preventing inflammation and/or inflammatory diseases or conditions such as asthma and/or inflammatory bowel disease.

The invention is at least partly predicated on the unexpected discovery that one or more tissue metalloprotease inhibitor proteins derivable or obtainable from hookworms including but not limited to, Ancylostoma caninum, may be useful for reducing, alleviating and/or preventing inflammation and/or inflammatory diseases or conditions such as asthma and/or inflammatory bowel disease in a subject.

In particular aspects, the invention contemplates use of (a) Ac-TMP-1 (SEQ ID NO:1) or a biologically active fragment or variant of Ac-TMP-1, (b) Ac-TMP-2 (SEQ ID NO:2) or a biologically active fragment or variant of Ac-TMP-2, or (c) a combination of (a) and (b) for reducing, alleviating and/or preventing inflammation and/or inflammatory disease or conditions such as asthma and/or inflammatory bowel disease.

Throughout this specification, unless the context requires otherwise, the words "comprise", "comprises" and "comprising" will be understood to imply the inclusion of a stated integer or group of integers but not the exclusion of any other integer or group of integers.

As used in this specification the indefinite articles "a" and "an" may refer to one entity or a plurality of entities (e.g. proteins) and are not to be read or understood as being limited to a single entity.

In one aspect, the invention provides a method of reducing or alleviating inflammation in a subject, the method including the step of administering to the subject a therapeutically effective amount of: (a) Ac-TMP-1 (SEQ ID NO:1) or a biologically active fragment or variant of Ac-TMP-1, (b) Ac-TMP-2 (SEQ ID NO:2) or a biologically active fragment or variant of Ac-TMP-2, or (c) a combination of (a) and (b).

In another aspect, the invention provides a method of preventing inflammation in a subject, the method including the step of administering to the subject a therapeutically effective amount of: (a) Ac-TMP-1 (SEQ ID NO:1) or a biologically active fragment or variant of Ac-TMP-1, (b) Ac-TMP-2 (SEQ ID NO:2) or a biologically active fragment or variant of Ac-TMP-2, or (c) a combination of (a) and (b).

By "reducing", as in reducing inflammation in a subject, is meant a lessening or shortening of a symptom, aspect, or characteristic associated with inflammation (e.g., redness, heat, swelling, and/or pain), or of the length of time a subject experiences a symptom, aspect, or characteristic associated with inflammation. Such reducing need not be absolute to be beneficial to the subject. By "alleviating", as in alleviating inflammation in a subject, is meant a reduction in the severity or seriousness of a symptom, aspect, or characteristic associated with inflammation (e.g., redness, heat, swelling, and/or pain). Such alleviating need not be absolute to be beneficial to the subject. Reduction and/or alleviation of inflammation in a subject can be determined using any methods or standards known to the ordinarily skilled artisan, including both qualitative and quantitative methods and standards.

It is to be understood that reducing or alleviating inflammation in a subject is a method of treating inflammation in the subject. As used herein, "treating" (or "treat" or "treatment") refers to a therapeutic intervention that ameliorates a sign or symptom of inflammation after it has begun to develop. The term "ameliorating," with reference to inflammation, refers to any observable beneficial effect of the treatment. The beneficial effect can be determined using any methods or standards known to the ordinarily skilled artisan.

As used herein, "preventing" (or "prevent" or "prevention") refers to a course of action (such as administering a therapeutically effective amount of Ac-TMP-1/Ac-TMP-2 or a biologically active fragment or variant thereof) initiated prior to the onset of a symptom, aspect, or characteristic of inflammation so as to prevent or reduce the symptom, aspect, or characteristic. It is to be understood that such preventing need not be absolute to be beneficial to a subject. A "prophylactic" treatment is a treatment administered to a subject who does not exhibit signs of inflammation or exhibits only early signs for the purpose of decreasing the risk of developing a symptom, aspect, or characteristic of inflammation.

As used herein, "inflammation" refers to the well known localised response to various types of injury or infection, which is characterised by redness, heat, swelling, and pain, and often also including dysfunction or reduced mobility. Inflammation, represents an early defence mechanism to contain an infection and prevent its spread from the initial focus. Major events in inflammation include dilation of capillaries to increase blood flow, changes in the microvasculature structure, leading to escape of plasma and proteins and leukocytes from the circulation, and leukocyte emigration from the capillaries and accumulation at the site of injury or infection.

Inflammation is often associated with, or secondary to, a disease, disorder and/or condition in a subject, including an immunological disease, disorder and/or condition (such as an autoimmune disease, disorder and/or condition) and allergic reactions. Exemplary immunological diseases, disorders and/or conditions include, without limitation, Addison's disease, ankylosing spondylitis, celiac disease, chronic inflammatory demyelinating polyneuropathy (CIDP), chronic recurrent multifocal ostomyelitis (CRMO), Crohn's disease, demyelinating neuropathies, glomerulonephritis, Goodpasture's syndrome, Graves' disease, Guillain-Barre syndrome, Hashimoto's encephalitis, Hashimoto's thyroiditis, hypogammaglobulinemia, idiopathic thrombocytopenic purpura (ITP), insulin-dependent diabetes (type1), juvenile arthritis, Kawasaki syndrome, multiple sclerosis, myasthenia gravis, postmyocardial infarction syndrome, primary biliary cirrhosis, psoriasis, idiopathic pulmonary fibrosis; Reiter's syndrome, rheumatoid arthritis, sarcoidosis, scleroderma, Sjogren's syndrome, systemic lupus erythematosus (SLE), thrombocytopenic purpura (TTP), ulcerative colitis, vasculitis, vitiligo, and Wegener's granulomatosis.

As will be understood by one of ordinary skill in the art, diseases of the digestive tract (e.g., chronic gastritis or an inflammatory bowel disease, such as, Crohn's disease or ulcerative colitis) and diseases of the respiratory system (e.g., asthma, emphysema, chronic bronchitis, and chronic obstructive pulmonary disease (COPD)) have an inflammatory component, and thus are particularly amendable to treatment using the disclosed methods.

Accordingly, in yet another aspect, the invention provides a method of treating and/or preventing an inflammatory bowel disease in a subject, the method including the step of administering to the subject a therapeutically effective amount of: (a) Ac-TMP-1 (SEQ ID NO:1) or a biologically active fragment or variant of Ac-TMP-1, (b) Ac-TMP-2 (SEQ ID NO:2) or a biologically active fragment or variant of Ac-TMP-2, or (c) a combination of (a) and (b).

In one embodiment, the inflammatory bowel disease is Crohn's disease or ulcerative colitis.

In a further aspect, the invention provides a method of treating and/or preventing asthma in a subject, the method including the step of administering to the subject a therapeutically effective amount of: (a) Ac-TMP-1 (SEQ ID NO:1) or a biologically active fragment or variant of Ac-TMP-1, (b) Ac-TMP-2 (SEQ ID NO:2) or a biologically active fragment or variant of Ac-TMP-2, or (c) a combination of (a) and (b).

As will also be understood by one of ordinary skill in the art, inflammation that is associated with, or secondary to, a disease, disorder and/or condition in a subject, often occurs when the disease, disorder and/or condition is refractory to a baseline therapy, for example, a baseline therapy comprising nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents), antibiotics, and combinations thereof. By "refractory" is intended resistance to treatment, particularly first line treatment.

The term "subject" includes both human and veterinary subjects. For example, administration to a subject can include administration to a human subject or a veterinary subject. Preferably, the subject is a human. However, therapeutic uses according to the invention may also be applicable to mammals such as domestic and companion animals, performance animals such as horses, livestock, and laboratory animals.

By "administration" is intended the introduction of a composition (e.g., a pharmaceutical composition comprising Ac-TMP-1/Ac-TMP-2, or a biologically active fragment or variant thereof) into a subject by a chosen route.

The term "therapeutically effective amount" describes a quantity of a specified agent sufficient to achieve a desired effect in a subject being treated with that agent. For example, this can be the amount of a composition comprising Ac-TMP-1 and/or Ac-TMP-2 (or a biologically active fragment or variant thereof) necessary to reduce, alleviate and/or prevent inflammation. In some embodiments, a "therapeutically effective amount" is sufficient to reduce or eliminate a symptom of inflammation. In other embodiments, a "therapeutically effective amount" is an amount sufficient to achieve a desired biological effect, for example an amount that is effective to decrease redness, heat, swelling, and/or pain associated with inflammation.

Ideally, a therapeutically effective amount of an agent is an amount sufficient to induce the desired result without causing a substantial cytotoxic effect in the subject. The effective amount of an agent, for example Ac-TMP-1 and/or Ac-TMP-2 (or a biologically active fragment or variant thereof), useful for reducing, alleviating and/or preventing inflammation will be dependent on the subject being treated, the type and severity of any associated disease, disorder and/or condition, and the manner of administration of the therapeutic composition.

A therapeutically effective amount of a composition comprising Ac-TMP-1 and/or Ac-TMP-2 (or a biologically active fragment or variant thereof) may be administered in a single dose, or in several doses, for example daily, during a course of treatment. However, the frequency of administration is dependent on the preparation applied, the subject being treated, the severity of inflammation, and the manner of administration of the therapy or composition.

By "Ac-TMP-1" is meant tissue metalloprotease inhibitor-1, a tissue inhibitor of metalloprotease from *Ancylostoma caninum* (dog hookworm). Ac-TMP-1 (UniProtKB/Swiss-Prot: # Q96318) is a 140 amino acid polypeptide.

By "Ac-TMP-2" is meant tissue metalloprotease inhibitor-2, a further tissue inhibitor of metalloprotease from *Ancylostoma caninum*. Ac-TMP-2 (UniProtKB/Swiss-Prot: # B1Q143) is a 244 amino acid polypeptide.

As used herein, "biologically active fragment" describes a portion or sub-sequence of Ac-TMP-1 or Ac-TMP-2, including a domain thereof, that has no less than 10%, preferably no less than 25%, more preferably no less than 50%, and even more preferably no less than 75%, 80%, 85%, 90%, or 95% of a biological activity of Ac-TMP-1 or Ac-TMP-2. Such activity may be evaluated using standard testing methods and bioassays recognizable by the skilled artisan in the field as generally being useful for identifying such activity.

A fragment of Ac-TMP-1 may constitute less than 120, less than 110, less than 100, less than 75, or less than 50 contiguous amino acids of a mature Ac-TMP-1 sequence. A fragment of Ac-TMP-2 may constitute less than 220, less than 200, less than 150, less than 120, less than 110, less than 100, less than 75, or less than 50 contiguous amino acids of a mature Ac-TMP-2 sequence. Multiple fragments of Ac-TMP-1 and/or Ac-TMP-2 are also contemplated.

By "domain" (of a protein) is meant that part of a protein that shares common structural, physiochemical and functional features, for example hydrophobic, polar, globular, helical, or netrin-like (NTR) domains, or properties, for example a protein binding domain, a receptor binding domain, a co-factor binding domain, and the like.

Also contemplated are variants of Ac-TMP-1 and Ac-TMP-2 comprising one or more amino acid substitutions, insertions and/or deletions in Ac-TMP-1 (or a fragment thereof) or Ac-TMP-2 (or a fragment thereof), as compared to wild-type Ac-TMP-1/Ac-TMP-2.

Typically, and in relation to proteins, a "variant" protein has one or more amino acids that have been replaced by different amino acids. It is well understood in the art that some amino acids may be changed to others with broadly similar properties without changing the nature of the activity of the protein (i.e., conservative substitutions).

It will also be appreciated that one or more amino acid residues of a reference sequence, such as Ac-TMP-1/Ac-TMP-2 (or a fragment thereof), may be modified or deleted, or additional sequences added, without substantially altering the biological activity of Ac-TMP-1/Ac-TMP-2 (or a fragment thereof). Such activity may be evaluated using standard testing methods and bioassays recognizable by the skilled artisan in the field as generally being useful for identifying such activity.

The term "variant" includes peptidomimetics and orthologs of Ac-TMP-1 and Ac-TMP-2. By "peptidomimetic" is meant a molecule containing non-peptidic structural elements that are capable of mimicking or antagonising the biological action(s) of a natural parent peptide. Examples of peptidomimetics include peptidic compounds in which the peptide backbone is substituted with one or more benzodiazepine molecules (sec, e.g., James et al., Science 260:1937-42, 1993) and "retro-inverso" peptides (see, e.g., U.S. Pat. No. 4,522,752). The term also refers to a moiety, other than a naturally occurring amino acid, that conforinationally and functionally serves as a substitute for a particular amino acid in a protein without adversely interfering to a significant extent with the function of the protein. Examples of amino acid mimetics include D-amino acids. Proteins substituted with one or more D-amino acids may be made using well known peptide synthesis procedures. Additional substitutions include amino acid analogs having variant side chains with functional groups, such as, for example, b-cyanoalanine, canavanine, djenkolic acid, norleucine, 3-phosphoserine, hornoserine, dihydroxyphenylalanine, 5-hydroxytryptophan, 1-methylhistidine, and 3-methylhistidine.

By "orthologs" of Ac-TMP-1 and Ac-TMP-2 is meant TMP orthologs from other intestinal helminths (i.e., hookworms, whipworms and roundworms), including human hookworms, such as, for example, *Necator americanus*, *Ancylostoma duodenale* and *Ancylostoma ceylanicum*, and pig whipworms, such as, for example, *Trichuris suis* and *Trichuris trichiura*.

In one embodiment, a protein variant or ortholog shares at least 70%, preferably at least 75%, 80% or 85% and more preferably at least 90%, 95%, 98%, or 99% sequence identity with a reference amino acid sequence such as SEQ ID NO:1 or SEQ ID NO:2.

Preferably, sequence identity is measured over at least 60%, more preferably over at least 75%, more preferably over at least 90% or more preferably over at least 95%, 98% or substantially the full length of the reference sequence.

In order to determine percent sequence identity, optimal alignment of amino acid and/or nucleotide sequences may be conducted by computerised implementations of algorithms (Geneworks program by Intelligenetics; GAP, BESTFIT, FASTA, and TFASTA in the Wisconsin Genetics Software Package Release 7.0, Genetics Computer Group, WI, USA) or by inspection and the best alignment (i.e., resulting in the highest percentage homology over the comparison window) generated by any of the various methods selected. Reference also may be made to the BLAST family of programs as for example disclosed by Altschul et al., *Nucl, Acids Res.* 25:3389-402, 1997.

A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

Variant proteins can be produced by a variety of standard, mutagenic procedures known to one of skill in the art. A mutation can involve the modification of the nucleotide sequence of a single gene, blocks of genes or a whole chromosome, with the subsequent production of one or more mutant proteins. Changes in single genes may be the consequence of point mutations, which involve the removal, addition or substitution of a single nucleotide base within a DNA sequence, or they may be the consequence of changes involving the insertion or deletion of large numbers of nucleotides.

Mutations occur following exposure to chemical or physical mutagens. Such mutation-inducing agents include ionizing radiation, ultraviolet light and a diverse array of chemical agents, such as alkylating agents and polycyclic aromatic hydrocarbons, all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation, which can subsequently be reflected at the protein level. Mutation also can be site-directed through the use of particular targeting methods.

Mutagenic procedures of use in producing Ac-TMP-1 and Ac-TMP-2 comprising one or more mutations include, but are not limited to, random mutagenesis (e.g., insertional mutagenesis based on the inactivation of a gene via insertion of a known DNA fragment, chemical mutagenesis, radiation mutagenesis, error prone PCR (Cadwell and Joyce, *PCR Methods Appl.* 2:28-33, 1992)) and site-directed mutagenesis (e.g., using specific oligonucleotide primer sequences that encode the DNA sequence of the desired mutation). Additional methods of site-directed mutagenesis are disclosed in U.S. Pat. Nos. 5,220,007; 5,284,760; 5,354,670; 5,366,878; 5,389,514; 5,635,377; and 5,789,166.

Isolated Ac-TMP-1 and Ac-TMP-2 (inclusive of fragments and variants) can be prepared by any suitable procedure known to those of skill in the art.

In one embodiment, Ac-TMP-1 and Ac-TMP-2 (inclusive of fragments and variants) are produced by chemical synthesis. Chemical synthesis techniques are well known in the art, although the skilled person may refer to Chapter 18 of CURRENT PROTOCOLS IN PROTEIN SCIENCE Eds. Coligan et. al., John Wiley & Sons NY (1995-2001) for examples of suitable methodology.

In another embodiment, Ac-TMP-1 and Ac-TMP-2, (inclusive of fragments and variants) are prepared as recombinant proteins.

While production of recombinant proteins is well known in the art, the skilled person may refer to standard protocols as for example described in Sambrook et al., MOLECULAR CLONING. A Laboratory Manual (Cold Spring Harbor Press, 1989), in particular Sections 16 and 17; CURRENT PROTOCOLS IN MOLECULAR BIOLOGY Eds. Ausubel et al., (John Wiley & Sons, Inc. 1995-1999), in particular Chapters 10 and 16; and CURRENT PROTOCOLS IN PROTEIN SCIENCE Eds. Coligan et al., (John Wiley & Sons, Inc. 1995-1999), in particular Chapters 1, 5 and 6.

Various combinations of one or more additional agents as known by one of skill in the art for reducing, alleviating and/or preventing inflammation (and/or for treating or preventing a disease, disorder and/or condition associated with inflammation) may be administered to a subject in need thereof in addition to a therapeutically effective amount of Ac-TMP-1 and/or Ac-TMP-2 (or a biologically active fragment or variant thereof). That is, one or more additional agents traditionally used for the treatment and/or prevention of inflammation may be administered to a subject in addition to a therapeutically effective amount of Ac-TMP-1 and/or Ac-TMP-2 (or a biologically active fragment or variant thereof).

For example, nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents) particularly anti-cytokine/cytokine receptor antibodies, antibiotics, and combinations thereof can be administered with Ac-TMP-1 and/or Ac-TMP-2 (or a biologically active fragment or variant thereof) in certain embodiments for reducing, alleviating and/or preventing inflammation.

In certain embodiments, the one or more additional agents provide a conserving effect on Ac-TMP-1 and/or Ac-TMP-2 (or a biologically active fragment or variant thereof). In further embodiments, the Ac-TMP-1 and/or Ac-TMP-2 (or a biologically active fragment or variant thereof) provide a conserving effect on the one or more additional agents. In still further embodiments, the one or more additional agents provide a complimentary effect to the action of the Ac-TMP-1 and/or Ac-TMP-2 (or a biologically active fragment or variant thereof), preferably eliminating or reducing the frequency or severity of (and/or preventing) one or more symptoms associated with inflammation.

As is well known to one of skill in the art, nonsteroidal anti-inflammatory drugs (NSAIDs), also referred to as nonsteroidal anti-inflammatory agents (NSAIAs), are drugs with analgesic, antipyretic and anti-inflammatory effects, and include salicylates (e.g., aspirin) and propionic acid derivatives (e.g., ibuprofen and naproxen.

Aminosalicylates are well known in the art for use in the treatment of inflammatory bowl disease (particularly ulcerative colitis), and include, for example, balsalazide, mesalazine, olsalazine, and sulfasalazine.

As is well known to one of skill in the art, corticosteroids are drugs that closely resemble cortisol, a hormone produced by the adrenal glands. Exemplary corticosteroids include, without limitation, cortisone, prednisone, prednisolone, and methylprednisolone.

Immunosuppressants are well known in the art for use in the treatment of inflammation associated with certain diseases or conditions, and include, for example, the drugs ciclosporin, azathioprine and mycophenolate.

As is well known to one of skill in the art, anti-cytokine/cytokine receptor agents (e.g., anti-TNFα agents, anti-IL-5 agents, anti-IL-13 agents, anti-IL-17 agents, and anti-IL-6R agents) include, without limitation, small molecule inhibitors and antibodies.

In some embodiments, the combination of Ac-TMP-1 and/or Ac-TMP-2 (or a biologically active fragment or variant thereof) and one or more additional. agents produces a synergistic effect in the treatment and/or prevention of inflammation. Accordingly, the present invention also includes a method of enhancing the therapeutic effectiveness of an agent in treating any condition for which such agents are used (e.g., inflammation and any associated disease, disorder and/or condition).

In one embodiment, the Ac-TMP-1 and/or Ac-TMP-2 (or a biologically active fragment or variant thereof) is administered prior to the administration of the one or more additional agents. In another embodiment, the Ac-TMP-1 and/or Ac-TMP-2 (or a biologically active fragment or valiant thereof) is administered after the administration of the one or more additional agents. In still another embodiment, the Ac-TMP-1 and/or Ac-TMP-2 (or a biologically active fragment or variant thereof) is administered simultaneously with the administration of the one or more additional agents. In yet another embodiment; administration of the Ac-TMP-1 and/or Ac-TMP-2 (or a biologically active fragment or variant thereof) and the administration of the one or more additional agents (either sequentially or concurrently) results in reduction or alleviation of inflammation that is greater than such reduction or alleviation from administration of either the Ac-TMP-1 and/or Ac-TMP-2 (or a biologically active fragment or variant thereof) or one or more additional agents in the absence of the other.

The Ac-TMP-1 and/or Ac-TMP-2 (or a biologically active fragment or variant thereof) and one or more additional agents can be administered by any conventional method/route available for use in conjunction with therapeutic compositions, as is well known to one of skill in the art. Such methods include, without limitation, administration by way of microneedle injection into specific tissue sites, such as described in U.S. Pat. No. 6,090,790, topical creams, lotions or sealant dressings applied to sites of inflammation, such as described in U.S. Pat. No. 6,054,122 or implants which release the Ac-TMP-1 and/or Ac-TMP-2 (or a biologically active fragment or variant thereof) such as described in International Publication. WO 99/47070.

In this regard, compositions comprising Ac-TMP-1 and/or Ac-TMP-2 (or a biologically active fragment or variant thereof) and, optionally, one or more additional agents, may be administered in association with, or as a component of; a biomaterial, biopolymer, inorganic material such as hydroxyapatite or derivates thereof, surgical implant, prosthesis, wound dressing, compress; bandage, or the like suitably impregnated, coated or otherwise comprising the composition.

Suitably, the composition comprises an appropriate pharmaceutically-acceptable carrier, diluent or excipient.

Preferably, the pharmaceutically-acceptable carrier, diluent or excipient is suitable for administration to mammals, and more preferably, to humans.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatin; talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates, and pyrogen-free water.

A useful reference describing pharmaceutically acceptable carriers, diluents and excipients is Remington's Pharmaceutical Sciences (Mack Publishing Co. NJ USA, 1991).

Any safe route of administration may be employed for providing a subject with compositions comprising Ac-TMP-1 and/or Ac-TMP-2 (or a biologically active fragment or variant thereof) and, optionally, one or more additional agents. For example, oral, rectal, parenteral, sublingual, buccal, intravenous, intra-articular, intra-muscular, intra-dermal, subcutaneous, inhalational, intraocular, intraperitoneal, intracerebroventricular, transdermal, and the like may be employed.

Dosage forms include tablets, dispersions, suspensions, injections, solutions, syrups, troches, capsules, suppositories, aerosols, transdermal patches, and the like. These dosage forms may also include injecting or implanting controlled releasing devices designed specifically for this purpose or other forms of implants modified to act additionally in this fashion. Controlled release of Ac-TMP-1 and/or Ac-TMP-2 (or a biologically active fragment or variant thereof) and, optionally, one or more additional agents, may be effected by coating the same, for example, with hydrophobic polymers including acrylic resins, waxes, higher aliphatic alcohols, polylactic and polyglycolic acids, and certain cellulose derivatives such as hydroxypropylmethyl cellulose. In addition, the controlled release may be affected by using other polymer matrices, liposomes and/or microspheres.

The above compositions may be administered in a manner compatible with the dosage formulation, and in such amount as is pharmaceutically/therapeutically-effective. The dose administered to a subject, in the context of the present invention, should be sufficient to effect a beneficial response (e.g., a reduction in inflammation) in a subject over an appropriate period of time. The quantity of Ac-TMP-1 and/or Ac-TMP-2 (or a biologically active fragment or variant thereof) to be administered may depend on the subject to be treated, inclusive of the age, sex, weight and general health condition thereof, factors that will depend on the judgement of a practitioner of ordinary skill in the art.

Compositions as described herein may also include expression vectors, such as viral vectors (e.g., vaccinia, adenovirus and adenovirus-associated viruses (AAV), retroviral and lentiviral vectors, and vectors derived from herpes simplex virus and cytomegalovirus. Gene therapy is also applicable in this regard, such as according to methods set forth in U.S. Pat. No. 5,929,040 and U.S. Pat. No. 5,962,427.

So that the invention may be readily understood and put into practical effect, the following non-limiting Examples are provided.

EXAMPLES

Example 1

Recombinant Ac-TMP-1 and Ac-TMP-2 Suppress IBD (TNBS Model)

Animals and TNBS-induced Colitis

Six week old male Swiss C57Bl/6 mice (weight 20-25 g, Animal Resources Centre, Perth, Western Australia) were allowed to adapt for seven days before they were used in the experiments. They were housed according to Australian animal rights and regulations standards. All procedures involving mice were approved by the James Cook University Animal Ethics Committee.

Colitis was induced by intraluminal injection of TNBS as described by Neurath et al. (*J Exp Med.* 182:1281-90, 1995). Briefly, mice were fasted for 24 hours with free access to drinking water. They were anesthetized i.p. by a mixture of ketamine (50 µg/kg) and xylazine (5 µg/kg). Next, 100 µL of a 2.5 mg TNBS in 45% ethanol solution was injected intrarectally through a flexible catheter of 3.2 cm length. After TNBS injection, mice were held upside down in a 45° position for one minute to prevent leakage of the TNBS solution and were replaced in their cages with free access to food and water afterward.

Experimental Protocol

On day 0, mice received a single intraperitoneal injection with 20 µg of AcES, Ac-TMP-1, Ac-TMP-2, denatured Ac-TMP-2 or a mock PBS injection. Five hours later, they received an intrarectal injection with 2 to 2.5 mg of TNBS in 45% ethanol, under a mild anaesthetic. From day 0 to day 3, mice were monitored daily for weight loss, mobility, general appearance, and presence of diarrhea. On day 3, mice were euthanized and colons were collected for assessment of inflammation (colon length, wall thickening, oedema, and ulceration).

Results

Figure 4:
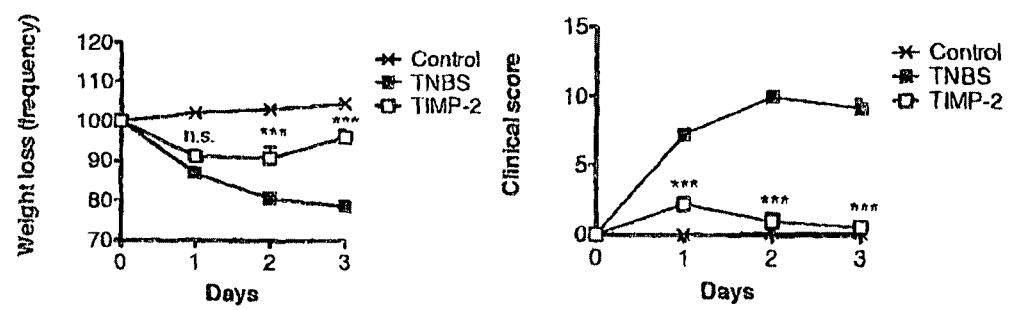
FIG. 4. Ac-TMP-2 protects mice against TNBS-induced model of colitis. Mice were treated with Ac-TMP-2 or vehicle (PBS) on day 0. Five hours later, they were anaesthetized and injected intra-rectally with 2.5 mg dose of TNBS in 45% ethanol. Weight, general appearance, stool and mobility were monitored daily. Mice treated with Ac-TMP-2 lost significantly less weight than the vehicle control group. The clinical score (combining the other monitored parameters) of the Ac-TMP-2-treated mice was also significantly less affected than the controls (*** P<0.001).
Figure 5:
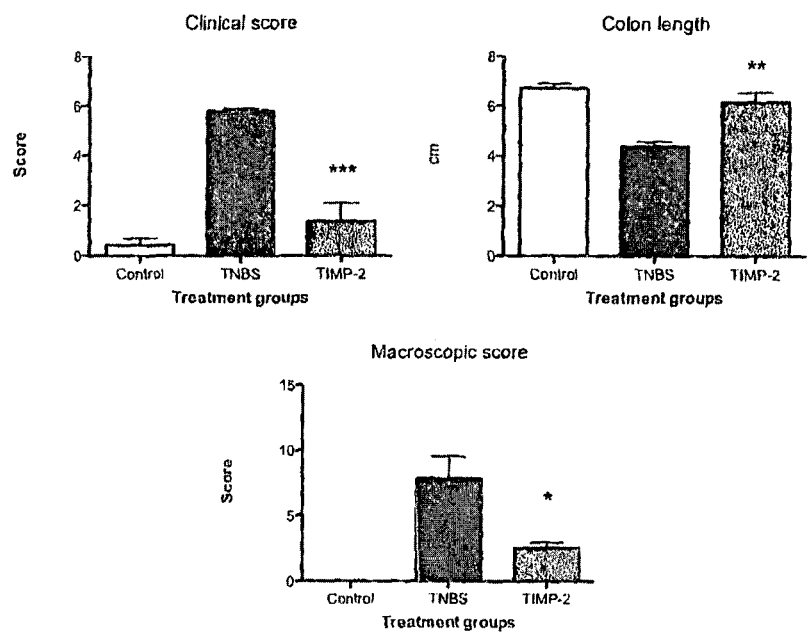
FIG. 5. Purified recombinant Ac-TMP-2 protects against TNBS-induced intestinal pathology. Briefly, mice received on day 0 a single intraperitoneal injection with 20 μg of Ac-TMP-2 (TIMP-2) or a mock PBS injection (TNBS). Five hours later, they received an intrarectal injection with 2.5 mg of TNBS in 45% ethanol, under a mild anaesthetic. On day 3, mice were sacrificed and clinical score, macroscopic score and colon length measured (see, Ruysscrs et al., *Inflamm. Bowel Dis.* 15:491-500, 2009 for methods). The control group (Control) did not receive any injections and were not administered TNBS.
Figure 6:
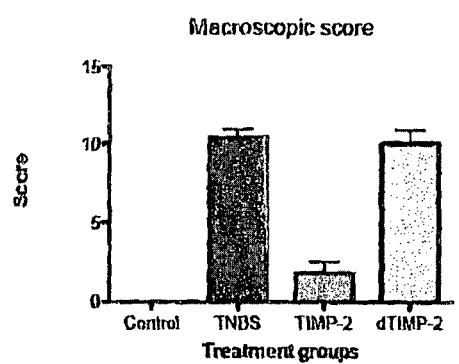
FIG. 6. Denaturation of Ac-TMP-2 with heat and protease treatment ablates its protective properties in a mouse model of TNBS colitis. Denaturation of Ac-TMP-2 by trypsin treatment and boiling abrogates Ac-TMP-2 induced protection in a mouse model of TNBS-induced colitis as shown here with the macroscopic score (combining colon adhesion, ulceration, oedema and wall thickening).

Recombinant Ac-TMP-1 and Ac-TMP-2 afforded excellent protection against weight loss in two separate TNBS colitis experiments (FIGS. 3 to 6). Ac-TMP-2 was further assessed for clinical and macroscopic scores and colon length and in this regard afforded significant reduction in intestinal pathology (FIGS. 4 to 6). Interestingly, denaturation of Ac-TMP-2 by trypsin and heating abrogated its protective activity in our mouse model of inflammatory colitis as assessed by macroscopic score (FIG. 6).

Example 2

Regulation of Experimental Asthma with Recombinant Ac-TMP-1

Animals and BSA-induced Asthma

Mice were sensitized with two intraperitoneal (i.p.) injections of 20 µg BSA in 2 mg of Aluminium hydroxide (Alum) on days 0 and 7. On days 14 to 21, mice were injected i.p. with 20 µg of either AcES or Ac-TMP-1. From days 18 to 21, mice were injected intranasally (i.n.) with 50 µg of BSA under a mild anaesthetic. On day 24, mice were sacrificed and tissue samples were collected.

Results

Figure 7:
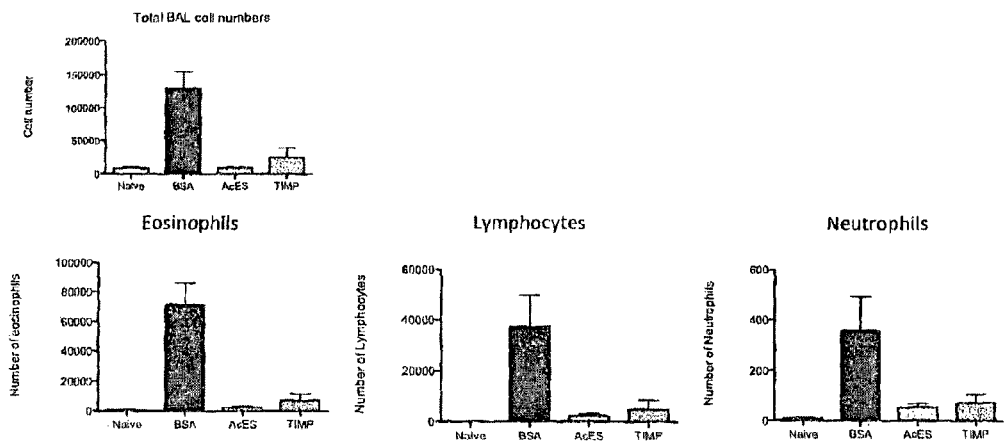
FIG. 7. Ac-TMP-1 protects against inflammation in a mouse model of allergic asthma. Bonchoalveolar lavage (BAL) infiltration is decreased in AcES (*Ancylostoma caninum* excretory/secretory proteins) and recombinant Ac-TMP-1 treated mice. Mice were sensitized with two intraperitoneal (i.p.) injections of 20 μg BSA in 2 mg of Aluminum hydroxide (Alum) on days 0 and 7. On days 14 to 21, mice were injected i.p. with 20 μg of either BSA, AcES or Ac-TMP-1 (TIMP). From day 18 to 21, mice were injected intranasally (i.n.) with 50 μg of BSA under a mild anaesthetic. On day 24, mice were sacrificed and BAL and lungs were collected. Briefly, mice were bled and a canula was inserted into the trachea. Lungs were washed three times with 1 ml of PBS. For differential BAL cell counts, cells were stained with anti-CCR3, anti-Gr1, anti-CD3, and anti-CD19 monoclonal antibodies and analysed by fluorescence-activated cell sorting (FACS) using a FACS canto II flow cytometer and FACS Diva software. Eosinophils were defined as $CCR3^+CD3^-CD19^-$, neutrophils as $Gr-1^{high} CCR3^-CD3^-CD19^-$, lymphocytes as $CD3^+CD19^+$.
Figure 8:
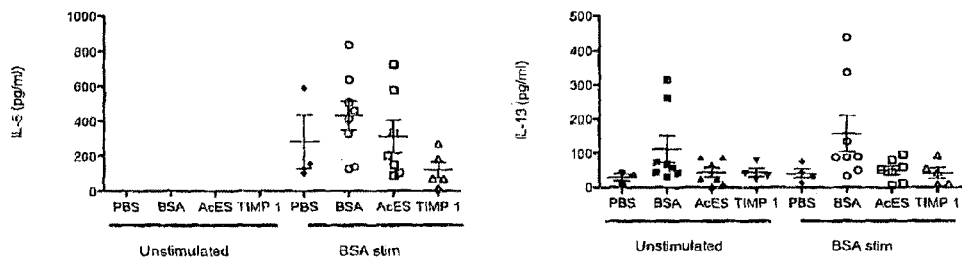
FIG. 8. IL-5 and IL-13 Th2 cytokines are decreased in AcES and recombinant Ac-TMP-1 treated mice. Lung samples were homogenized in calcium and magnesium-free Hanks balanced salt solution containing 5% fetal calf serum. Cells were restimulated in vitro with 1 mg/ml of AcES or Ac-TMP-1, or left unstimulated for three days at 37° C. Multiplex IL-5, and IL-13 analyses were performed with cytometric bead array using FACS array.
Figure 9:
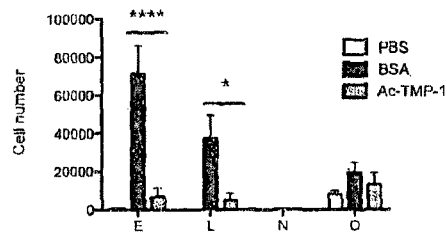
FIG. 9. Repeat experiment showing the robustness of the protection mediated by Ac-TMP-1 in a mouse model of allergic asthma. Bonchoalveolar lavage (BAL) infiltration is decreased in Ac-TMP-1 treated mice. BAL cells were collected and analysed by (FACS). Eosinophils were defined as $CCR3^+CD3^-CD19$, neutrophils as $Gr-1^{high} CCR3^-CD3^-CD19^-$, lymphocytes as $CD3^+CD19^+$. Treatment with Ac-TMP-1 significantly reduces the infiltration of Th2 cells such as eosinophils and lymphocytes into the airways.
Figure 10:
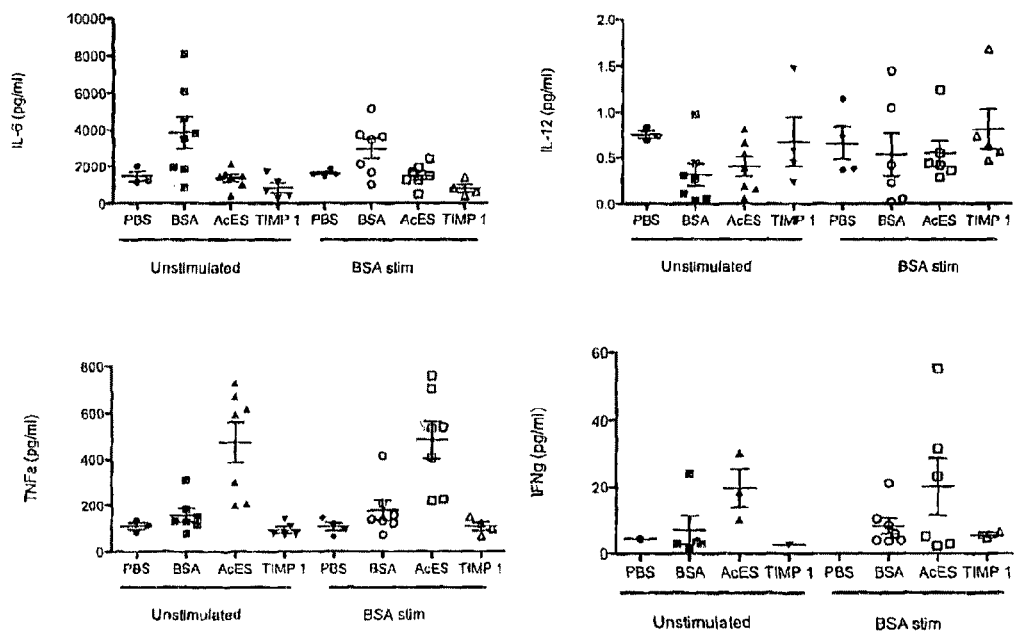
FIG. 10. Pro-inflammatory cytokines IL-6, TNFα, and IFNγ are decreased in recombinant Ac-TMP-1 treated mice. Lung samples were homogenized in calcium and magnesium-free Hanks balanced salt solution containing 5% fetal calf serum. Cells were restimulated in vitro with 1 mg/ml of AcES or Ac-TMP-1, or left unstimulated for three days at 37° C. Multiplex IL-6, IL-12, TNFα, and IFNγ analyses were performed with cytometric bead array using FACS array.
Figure 11:
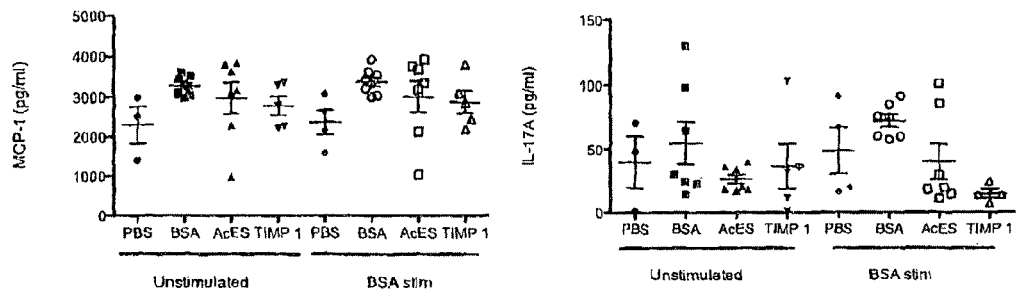
FIG. 11. IL-17A is decreased in recombinant Ac-TMP-1 treated mice. Lung samples were homogenized in calcium and magnesium-free Hanks balanced salt solution containing 5% fetal calf serum. Cells were restimulated in vitro with 1 mg/ml of AcES or Ac-TMP-1, or left unstimulated for 3 days at 37° C. Multiplex IL-17A and MCP-1 were analyzed using cytometric bead array.

To investigate whether AcES or Ac-TMP-1 could prevent allergic airway inflammation in mice, BALB/c mice were treated daily with AcES or Ac-TMP-1 (20 µg i.p.) for four consecutive days before the challenge and four more days in concomitance to the challenge. Compared to the PBS mock injection group, AcES and Ac-TMP-1 treated mice exhibited a significantly reduced eosinophilia, perivascular and peribronchial cellular infiltration of the lungs (FIGS. 7 and 9). Compared to the naïve group, PBS-treated BSA-challenged mice exhibited increased levels of Th2 cytokines such as interleukin (IL)-5 and IL-13, as well as markers of inflammation such as IL-6 (FIGS. 8 and 10). We found that AcES and Ac-TMP-1 treatments resulted in one- to five-fold less (respectively) IL-5, and 2-fold less IL-13 in the lungs (FIG. 8). Inflammatory cytokine IL-6 was also 2 to 3-fold decreased in mice treated with AcES or Ac-TMP-1 (FIG. 10). Interestingly, while pro-inflammatory cytokines TNFα or IFNγ are not directly associated with asthma-induced inflammation, levels were 3- and 5-fold increased (respectively) in AcES-treated mice (FIG. 10). However, levels remained unaffected by the Ac-TMP-1 treatment, suggesting that Ac-TMP-1 is well tolerized and does not induce inflammatory responses. IL-12 and MCP-1 levels remained unaffected by the AcES or Ac-TMP-1 treatments, meaning that the prevention of BSA-induced inflammation does not require the induction of Th1 response and does not affect monocyte chemotaxis (FIGS. 10 and 11). Surprisingly, AcES or Ac-TMP-1 treatments induced a 2 to 3-fold decrease in IL-17A levels in the lungs, which in high levels has been reported to be associated with severe asthma-induced inflammation and airway hyper-responsiveness (FIG. 11). Taken together, these results illustrate that AcES and Ac-TMP-1 reduce significantly BSA-induced airway infiltration of eosinophils and lymphocytes, but also Th2 and Th17 responses, as well as pro-inflammatory cytokines such as IL-6.

Example 3

Regulation of Experimental Asthma with Recombinant Ac-TMP-1/2

Animals and OVA-induced Asthma

Sensitization was performed by two intraperitoneal (i.p.) injections of 20 µg of OVA in 2 mg of Aluminum hydroxide (Alum) (Pierce) at day 0 and 7. On days 14 to 21, mice were injected i.p. with 20 µg of either Ac-TMP-1 or Ac-TMP-2. From day 18 to 22, mice were exposed to OVA (0.25%) aerosols for 20 min using an ultrasonic nebulizer. Mice were analyzed on day 24.

On day 24, mice were sacrificed and bronchoalveolar lavages were collected. Cells were counted and stained with anti-Siglec F or anti-CCR3, anti-Gr1, anti-CD3, and anti-CD19 monoclonal antibodies and analysed by fluorescence-activated cell sorting (FACS) using a FACS canto II flow cytometer and FACS Diva software. Eosinophils were defined as CCR3+ or SiglecF+ CD3− CD19−, neutrophils as Gr-1$^{high}$ SiglecF−CD3−CD19−, lymphocytes as CD3+ CD19+.

On day 24, mice were sacrificed and peritoneal lavages were collected. Briefly, the peritoneum was washed twice times with 5 ml of ice cold HBSS implemented with 5% FCS. For differential PL cell counts, cells were stained with anti-CCR3, anti-Gr1, anti-CD3, and anti-CD19 monoclonal antibodies and analysed by fluorescence-activated cell sorting (FACS) using a FACS canto II flow cytometer and FACS Diva software.

Lung samples from each individual mouse were taken and homogenized in calcium and magnesium-free Hanks balanced salt solution containing 5% fetal calf serum. Cells were either stimulated again in vitro with 1 mg/mL of Ac-TMP-1 or left unstiniulated for three days at 37° C. Supernatants from these cultures were collected and IL-5, IL-10, IL-13, MCP-1 and IL-17A levels were assessed by cytomeric bead array and FACS analysis. Alternatively, whole protein extract were prepared from snap frozen lungs of individual mice in calcium and magnesium-free Flanks balanced salt solution, containing proteinase cocktail inhibitor. Extract contents were analyzed by CBA.

Results

Figure 12:
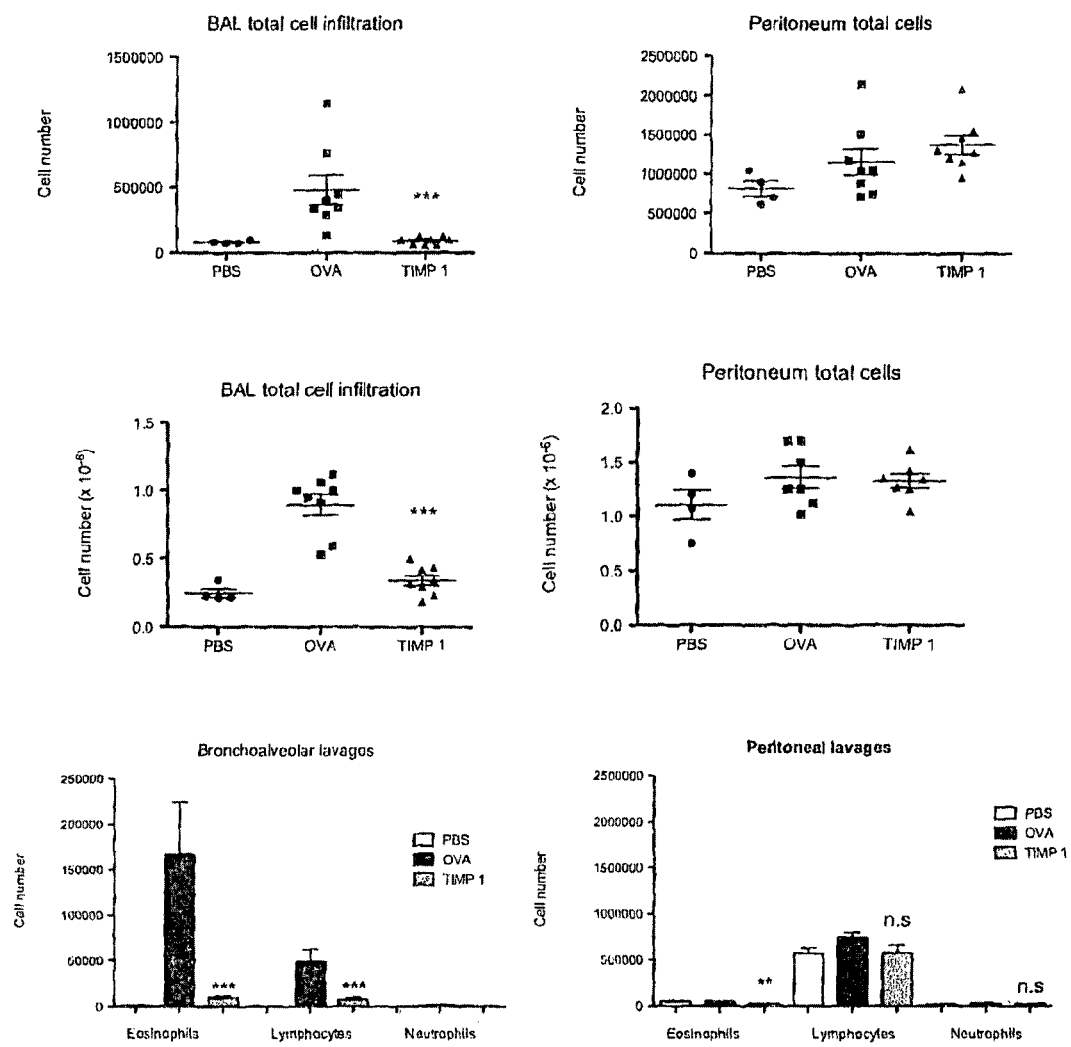
FIG. 12. Ac-TMP-1 prevents OVA-induced lung cellular infiltration in a mouse model of asthma. Bronchoalveolar lavage samples from untreated OVA-challenged mice demonstrate a significant elevation in cell number when compared to naïve (PBS) mice. Treatment with Ac-TMP-1, however, significantly reduces total cell infiltration in bronchoalveolar lavage samples from OVA-challenged mice. In keeping with the elevated total cell counts, the differential cell counts from the BAL samples of untreated OVA-challenged mice exhibit a significant elevation in eosinophils and lymphocytes. Treatment with Ac-TMP-1, however, prevented this eosinophilic and lymphocytic infiltration into the lungs of OVA-challenged mice. There was no increase in total cell number, eosinophils, lymphocytes or neutrophils from the peritoneal lavages of OVA-challenged mice. Unlike in the lung, Ac-TMP-1 did not alter total peritoneal cell counts. It did, however, cause a significant reduction in peritoneal eosinophils. Data from replicate experiments is provided for BAL and peritoneal lavage total cell counts.
Figure 15:
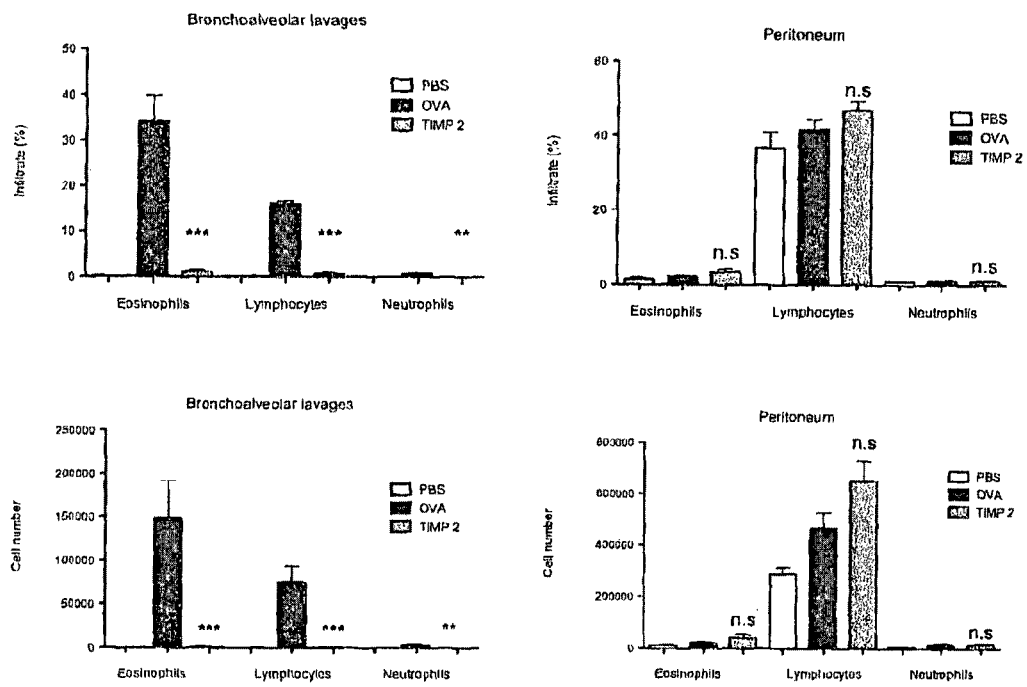
FIG. 15. Ac-TMP-2 prevents OVA-induced lung cellular infiltration in a mouse model of asthma. Bronchoalveolar lavage samples from untreated OVA-challenged Mice demonstrate a significant elevation in eosinophils, lymphocytes and neutrophils when compared to naïve (PBS) mice. Conversely, no such elevation is observed in the peritoneal lavage samples from these mice. Treatment with Ac-TMP-2 significantly prevented this eosinophilic, lymphocytic and neutrophilic infiltration into the lungs of OVA-challenged mice. Ac-TMP-2, however, had no significant effect on differential cell counts from peritoneal lavage samples.
Figure 16:
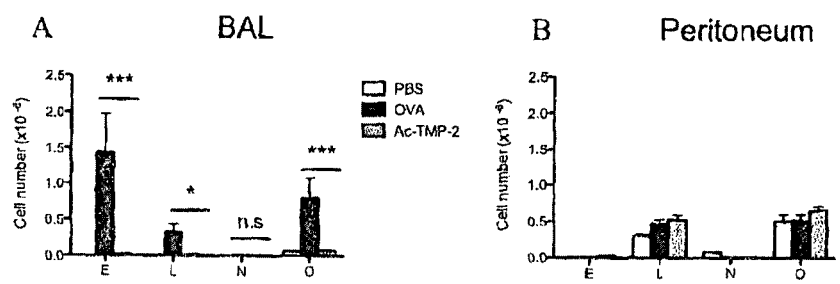
FIG. 16. Ac-TMP-2 protects mice against OVA-induced lung cellular infiltration. (A) and (B) Differential cell count in the bronchoalveolar (A) and peritoneal (B) lavage fluids obtained. BALF were obtained after inserting a cannula into the trachea and washing with 3×1 mL PBS. Peritoneal lavages were obtained by injecting 3×5 mL of RPMI supplemented with 5% FCS into the peritoneum. Cells were stained with antibodies and analyzed by Flow Cytometry (FACSCanto II). Numbers of eosinophils (B) and lymphocytes (L) in bronchoalveolar lavage fluid (BALF) were highly significantly reduced ($P<0.001$) in mice treated with Ac-TMP-2 prior to OVA aerosol challenges. (B) No such differences in cell numbers were detected at the site of Ac-TMP-2 injection (peritoneum), highlighting the fact that protection against cellular infiltration is restricted to sites of inflammation. Data from replicate experiments is provided for BAL and peritoneal lavage total cell counts.

Previous results generated in our laboratory revealed that the complex composition of ACES induces a variety of T cell responses, including a robust Th2 response associated with a peritoneal infiltration of eosinophils. In order to verify that Ac-TMP-1 or Ac-TMP-2 did not induce a stronger chemotactic signal in the peritoneum than the airways, in parallel to bronchoalveolar lavages, peritoneal lavages of naïve mice, mice treated with PBS-mock injections, Ac-TMP-1, or Ac-TMP-2 were collected and analysed by FACS (FIGS. 12, 15 and 16). While the mice treated with Ac-TMP-1 and Ac-TMP-2 showed a significantly decreased eosinophilia in the airways as compared to the mock injection group, there was no infiltration of eosinophils in the peritoneum (FIGS. 12, 15 and 16), indicating that Ac-TMP-1 and Ac-TMP-2 prevent the induction of eosinophils at sites of allergic or inflammatory response only.

Figure 13:
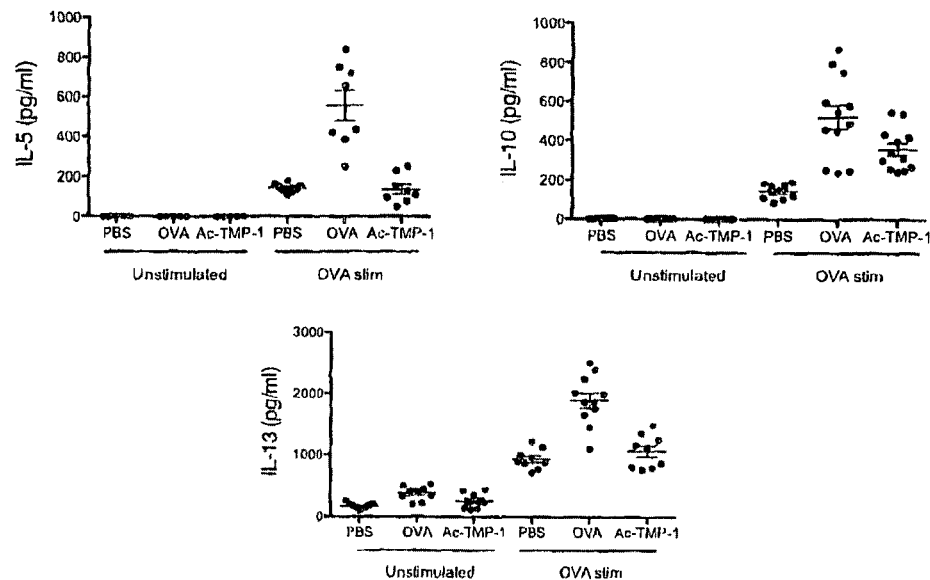
FIG. 13. Th2 cytokines are decreased in the lung of Ac-TMP-1 treated mice. Whole protein extracts were prepared from the lungs of individual mice and analyzed for IL-5, IL-10 and IL-13 content by Cytometric Bead Array (CBA). Levels of IL-5, IL-10 and IL-13 are significantly reduced upon treatment with. Ac-TMP-1. Treatment with Ac-TMP-1 lowered levels of these cytokines confirming a decrease in inflammation as seen in FIG. 12.
Figure 14:
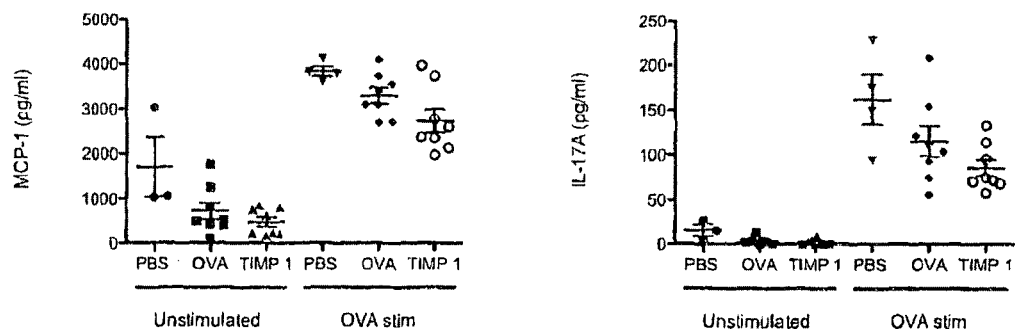
FIG. 14. Pro-inflammatory cytokines are decreased in the lung of Ac-TMP-1 treated mice. Whole protein extracts were prepared from the lungs of individual mice and analyzed for MCP-1 and IL-17A content by Cytometric Bead Array (CBA). Both cytokines were reduced in the presence of Ac-TMP-1.
Figure 17:
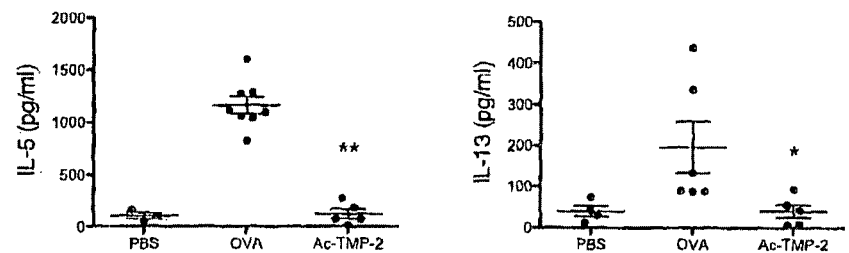
FIG. 17. Th2 cytokines are decreased in the lung of Ac-TMP-2 treated mice. Whole protein extracts were prepared from the lungs of individual mice and analyzed for IL-5 and IL-13 content by Cytometric Bead Array (CBA). Levels of both IL-5 and IL-13 are significantly reduced upon treatment with Ac-TMP-2.
Figure 18:
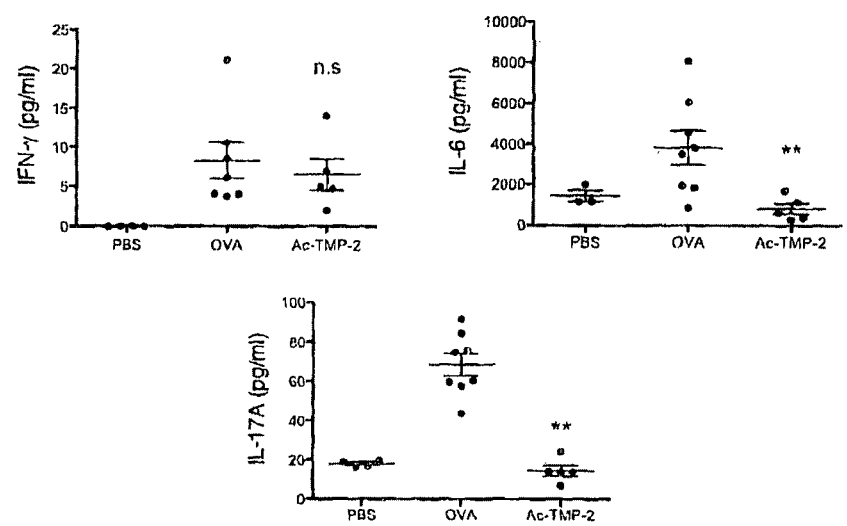
FIG. 18. Pro-inflammatory cytokines IL-6 and IL-17A are decreased in recombinant Ac-TMP-2 treated mice. Whole protein extracts were prepared from the lungs of individual mice and analyzed for IFN-γ, IL-6 and IL-17A content by Cytometric Bead Array (CBA). No change was observed in the levels of IFN-γ, which is to be expected in our model of asthma, however both levels of IL-6 and IL-17A were significantly decreased upon treatment with Ac-TMP-2.

Lung cells from OVA-challenged mice demonstrated increased levels of IL-5, IL-10 and IL-13 secretion with OVA stimulation in vitro (FIG. 13). Supernatant levels of MCP-1 and IL-17A, on the other hand, were similarly elevated in both PBS-mock and OVA-challenged Mouse lung cells when stimulated with OVA (FIG. 14). In accordance with the bronchoalveolar lavage findings, levels of Th2 cytokines, IL-5, IL-10 and IL-13, and the pro-inflammatory cytokines, MCP-1 and IL-17A, were reduced in the OVA-stimulated lung cells from Ac-TMP-1 treated mice (FIGS. 13 and 14). Similarly, lung cytokine content was significantly decreased in mice treated with Ac-TMP-2 (FIGS. 17 and 18) suggesting that Ac-TMP-2 efficiently suppresses Th2 and pro-inflammatory cytokines such as IL-6 and IL-17A.

Example 4

Regulation of Experimental Chronic Asthma with Recombinant Ac-TMP-2

Animals and OVA-induced Chronic Asthma

Sensitization was performed by two intraperitoneal (i.p.) injections of 20 µg of OVA in 2 mg of Aluminum hydroxide (Alum) (Pierce) at day 0 and 7. On days 14 to 18, mice were injected i.p. with either 20 µs of Ac-TMP-2 or a PBS control solution. From days 17 to 20 and days 36 to 40, mice were exposed to OVA (0.25%) aerosols for 20 min using an ultrasonic nebulizer. On days 36 to 40, a group of previously Ac-TMP-2 treated mice, were again injected i.p. with 20 µg of Ac-TMP-2. The remaining mice, whether previously treated with Ac-TMP-2 or not, were injected i.p. with a PBS control solution. Mice were analysed on day 42 for airway inflammation.

Results

Figure 19:
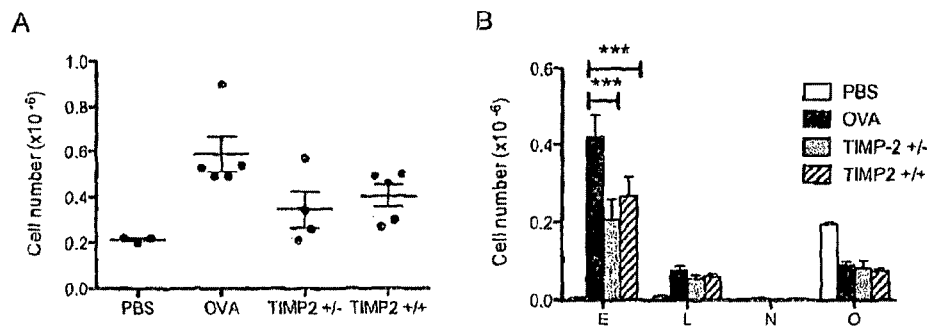
FIG. 19. Ac-TMP-2 decreases airway infiltration in a mouse model of chronic asthma. In order to investigate the long-term protection and the efficacy of Ac-TMP-2 on chronic airway inflammation, mice were sensitized to OVA and challenged twice with 5 daily aerosols of OVA, with a resting period of 3 weeks between challenges. (A) Total cellular airway infiltration obtained as described previously. (B) Differential cell count. Whether Ac-TMP-2 was administered during the first challenge (+/−) or both sets of challenges (+/+), mice were significantly protected from eosinophilic airway infiltration ($P<0.001$).

To assess whether Ac-TMP-2, either administered only during the first OVA challenge (+/−) or during both sets of OVA challenges (+/+), decreased airway inflammation in a mouse model of chronic asthma, bronchoalveolar lavages of naïve mice, mice treated with PBS-mock injections, or mice treated with Ac-TMP-2 (+/− and +/+) were collected and analysed by FACS (FIG. 19). Regardless of whether Ac-TMP-2 was administered during the first challenge (+/−) or both challenges (+/+), treated mice demonstrated a significant reduction in both total cellular and eosinophilic airway infiltration when compared to mice treated with PBS-mock injections, in this model of OVA-induced chronic asthma (FIG. 19).

Example 5

Regulation of Experimental Asthma with Recombinant Ac-TMP-2

Animals and OVA-induced Asthma

Sensitization was performed by two intraperitoneal (i.p.) injections of 20 µg of OVA in 2 mg of Aluminum hydroxide (Alum) (Pierce) at day 0 and 7. On days 14 to 18, one cohort of OVA-sensitized mice were intranasally (i.n.) injected with 20 µg of Ac-TMP-2 (preventative treatment). From day 22 to 26, OVA-sensitized mice were exposed to OVA (0.25%) aerosols for 20 min using an ultrasonic nebulizer. On days 24 to 28, a second cohort of OVA-sensitized mice were intranasally (i.n.) injected with 20 µg of, Ac-TMP-2 (curative treatment). Mice were analysed on day 30 for airway inflammation.

Results

Figure 20:
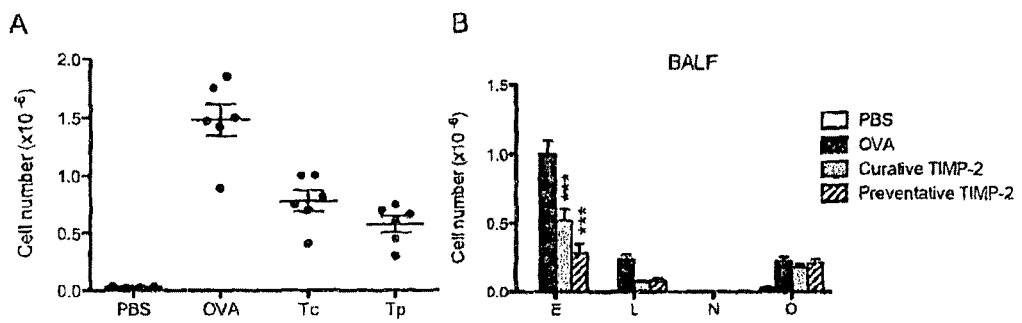
FIG. 20. Preventative and curative Ac-TMP-2 treatment in OVA-induced asthma. In order to assess whether Ac-TMP-2 could be administered locally (via intranasal injections) and whether it could prevent the development of inflammation when administered in a preventative (before the OVA challenges) or in a curative (after the OVA challenges) fashion, mice were sensitized to OVA and were either treated with 4 in. injections of Ac-TMP-2 a week before challenging the mice to OVA aerosols (preventative) or with 4 in. injections of Ac-TMP-2 two days after the challenges had begun (curative). (A) Total cellular airway infiltration obtained as described previously. (B) Differential cell count. Whether mice were treated with Ac-TMP-2 in a preventative or curative manner, both groups were significantly protected from eosinophilic airway infiltration ($P<0.001$).

To determine whether Ac-TMP-2 administered locally via intranasal injections could attenuate airway inflammation when given in a preventative (Tp, before the OVA-challenge) or a curative (Te, after the OVA-challenge) manner, bronchoalveolar lavages of naïve mice, OVA-challenged mice treated with PBS-mock injections, or OVA-challenged mice treated with Ac-TMP-2 (Tc and Tp) were collected and analysed by FACS from which total and differential cell counts were derived (FIG. 20). Regardless of whether mice were treated in a preventative or curative fashion, intranasal Ac-TMP-2 significantly attenuated both total and eosinophilic airway cellular infiltration (FIG. 20). Importantly, these data highlight that Ac-TMP-2 may also be administered locally and not just parenterally to prevent airway inflammation in this murine model of asthma.

Figure 21:
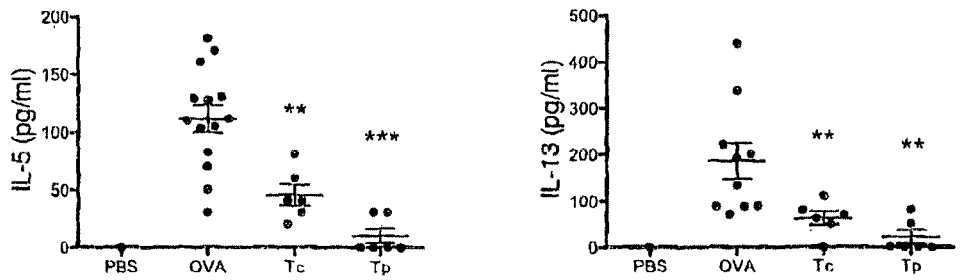
FIG. 21. Th2 cytokines are reduced in BALF in preventative and curative Ac-TMP-2 treatment. Whole protein extracts were prepared from the lungs of individual mice and analyzed for interleukin-5 and IL-13 content by Cytometric Bead Array (CBA). Levels of both IL-5 and IL-13 were significantly reduced upon both preventative and curative treatment with Ac-TMP-2 ($P<0.01$ and $P<0.001$).

Whole protein extracts from the lungs of naïve mice, OVA-challenged mice treated with PBS-mock injections, or OVA-challenged mice treated with Ac-TMP-2 (Tc and Tp) were prepared and analysed for the Th2 cytokines, IL-5 and IL-13, by Cytometric Bead Array (CBA). Compared to the naïve group, PBS-treated OVA-challenged mice demonstrated significantly elevated levels of both IL-5 and IL-13 (FIG. 21). We found that treatment with Ac-TMP-2, in either a preventative or curative manner, significantly reduced IL-5 and IL-13 levels (FIG. 21). Taken together these findings illustrate that Ac-TMP-2 when administered intranasally significantly reduced OVA-induced eosinophilic airway infiltration and the associated Th2 inflammatory response.

Example 6

Regulation of Regulatory T Cells (Tregs) with Recombinant Ac-TMP-2

Animals and Regulatory T Cells

Mice were injected intraperitoneally with either Ac-TMP-2 (20 µg) or PBS for 6 days and mesenteric lymph nodes (MLN), spleen and small intestine lamina propria (LP) were harvested and analysed for the presence of Tregs. Individual cells from each tissue were isolated and stained for the Treg markers CD4, CD25 and Foxp3 and subsequently analysed by flow cytometry. Tregs from the MLN, spleen and pyloric lymph node (PLN) and LP were further stained with CCR9 antibody and analysed by flow cytometry to determine their tissue of origin.

Results

Figure 22:
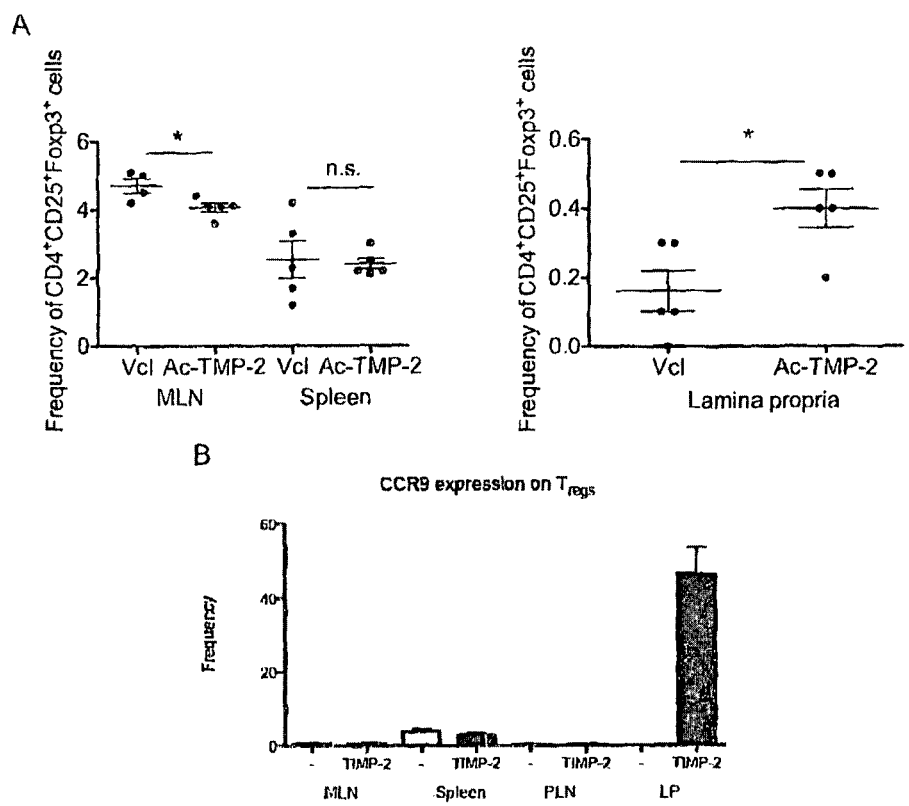
FIG. 22. Ac-TMP-2 induces the generation of regulatory T cells that accumulate in the mucosa. Naïve mice were treated with i.p. injections of Ac-TMP-2 or PBS (vcl) for 6 days and mesenteric lymph nodes (MLN), spleen and small intestine lamina propria were analyzed for the presence of Tregs. (A) Cells were prepared from the mesenteric lymph nodes, spleen and small intestine lamina propria of mice treated or not with Ac-TMP-2. (13) Cells from MLN, spleen, pyloric lymph node (PLN) and small intestine lamina propria (LP) were stained with CCR9 antibodies, a marker exclusively expressed on cells generated in the MLN, and analyzed by Flow Cytometry. Data show that Ac-TMP-2 induces a significant accumulation of Tregs in the small intestinal mucosa and that the expression of CCR9 on the Tregs found in the lamina propria suggests that they originate from the mesenteric lymph nodes ($P<0.05$).

The administration of Ac-TMP-2 to naïve mice significantly induced the recruitment of Tregs into the lamina propria of the small intestine (FIG. 22). Conversely, a significant decrease in the frequency of Tregs from the mesenteric lymph nodes (MLN) was observed with Ac-TMP-2 treatment (FIG. 22). These data suggest a migration pattern of Tregs from the MLN towards the mucosa of the intestine. In support of this, sixty percent of the lamina propria Tregs expressed the chemokine receptor CCR9, indicating that they have been imprinted in the gut-associated draining lymph nodes (i.e. MLN) (FIG. 22). This observation coincides with data suggesting that Tregs generated in the MLN accumulate in the mucosa in order to maintain tolerance to ubiquitous antigens (Navarro et al. *Mucosal Immunol.* 4:53-65 2011).

Example 7

Regulation of Regulatory T Cells (Tregs) in Experimental Asthma with Recombinant Ac-TMP-2

Animals and OVA-induced Asthma

Figure 23:
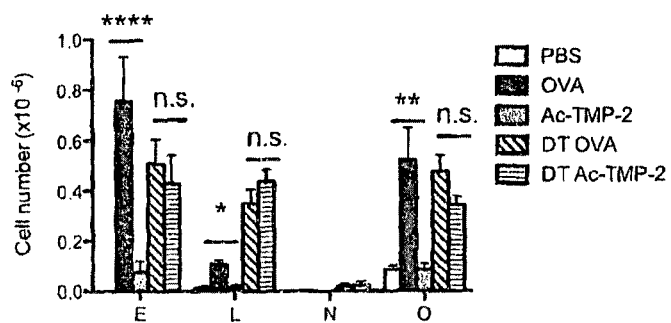
FIG. 23. Ac-TMP-2-mediated protection against inflammation is dependent on regulatory T cells (Tregs). To investigate the importance Tregs in the protection induced by Ac-TMP-2 in our model of experimental asthma, we selectively depleted Tregs using diphtheria toxin (DT) in transgenic mice (DEREG mice) engineered to express the DT receptor under the Foxp3 promoter, which is the transcription factor for Tregs. Wild-type controls (C57Bl/6) and DEREG mice were sensitized and challenged with OVA. Mice treated with Ac-TMP-2 that received injections of DT to deplete Tregs (DEREG mice) had comparable levels of airway inflammation and BAL infiltration to untreated mice challenged with OVA and exposed to DT. These results suggest Tregs play an essential role in the suppression of inflammation by Ac-TMP-2 in our mouse model of asthma.
Figure 24:
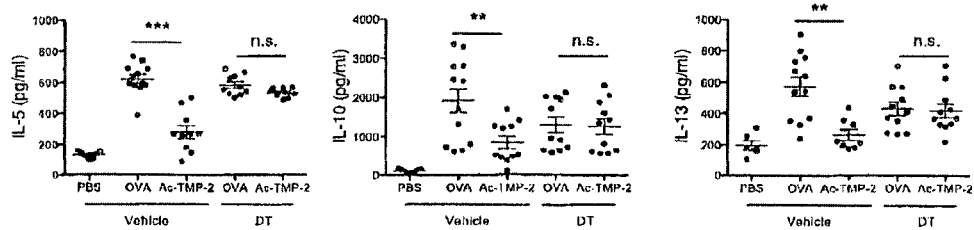
FIG. 24. Tregs are important in, the suppression of Th2 cytokines in Ac-TMP-2 treated mice. Whole protein extracts were prepared from the lungs of individual mice and analyzed for IL-5, IL-10 and IL-13 content by Cytometric Bead Array (CBA). Levels of IL-5, IL-10 and IL-13 were significantly reduced upon treatment with Ac-TMP-2 in the wild-type mice, while there were no significant differences in the DEREG mice in which the Tregs were depleted treated with Ac-TMP-2 ( P<0.01 and * P<0.001).
Figure 25:
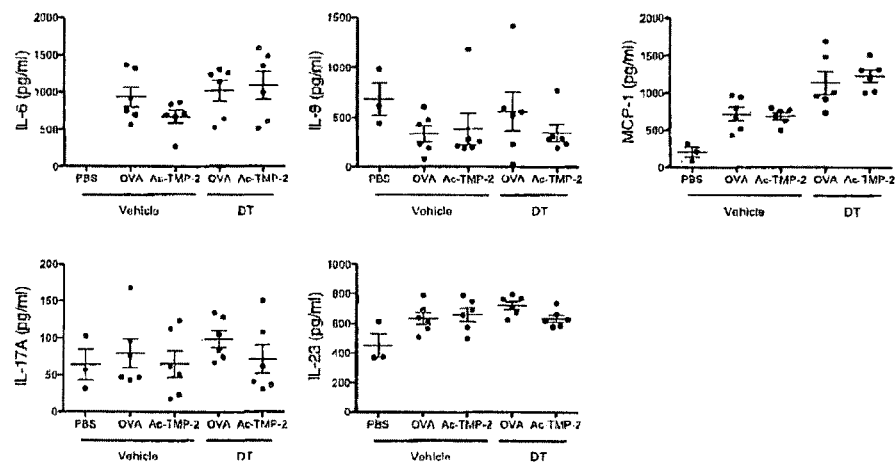
FIG. 25. Tregs induced by Ac-TMP-2 are important in the suppression of pro-inflammatory cytokines. Whole protein extracts were prepared from the lungs of individual mice and analyzed for IFN-γ, interleukin-6, IL-9 and IL-17A, IL-23, and MCP-1 content by Cytometric Bead Array (CBA). Levels of IFN-γ were below detection levels (data not shown) and only IL-6 was down regulated in the wild-type mice in the presence of Ac-TMP-2. As expected, Th-1 and Th-17 cytokine levels remained low or, unaltered in our mouse model of asthma.

To investigate the contribution of Tregs to the protection induced by Ac-TMP-2 in our model of OVA-induced experimental asthma, we selectively depleted Tregs in mice prior to OVA sensitization and exposure. This depletion was achieved by using diphtheria toxin (DT) in transgenic mice engineered to express the DT receptor under the Treg-specific Foxp3 promoter (DEREG mice; Lahl and Sparwasser *Methods Mol Biol.* 707:157-72 2011). Wild-type and DEREG mice were then sensitized by two i.p. injections of 20 µg of OVA in 2 tug of Aluminum hydroxide (Alum) (Pierce) at day 0 and 7. On days 14 to 21, sensitized wild-type and DEREG mice were injected i.p. with either 20 µg Ac-TMP-2 or a PBS control solution. From day 18 to 22, OVA-sensitized mice were exposed to OVA (0.25%) aerosols for 20 min using an ultrasonic nebulizer. Mice were analysed on day 24 for airway inflammation. Bronchoalveolar lavages were collected from naïve wild-type mice and sensitized wild-type and DEREG mice treated with either PBS-Mock injections or Ac-TMP-2, and analysed by FACS from which differential cell counts were derived (FIG. 23). Whole protein extracts were prepared from the lungs of mice from each treatment cohort and analysed for the protein expression of Th2-associated cytokines (FIG. 24) and pro-inflammatory cytokines (FIG. 25).

Results

Similar to Example 3 above, Ac-TMP-2 treatment significantly reduced airway inflammation in OVA-challenged wild-type mice (FIG. 23). Conversely, OVA-challenged DEREG mice treated with Ac-TMP-2 demonstrated comparable levels Of bronchoalveolar infiltration to untreated DEREG mice challenged with OVA (FIG. 23). In keeping with these findings, levels of the Th2 cytokines, IL-5, IL-10 and IL-13, and the pro-inflammatory IL-6 were significantly reduced in OVA-challenged wild-type mice, but not OVA-challenged DEREG mice, upon treatment with Ac-TMP-2 (FIGS. 24 and 25). Taken together, these results suggest that Tregs play an integral role in the anti-inflammatory action of Ac-TMP-2 in our mouse model of asthma.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

The invention claimed is:
1. A method for reducing or alleviating inflammation in a subject, the method including the step of administering to the subject a therapeutically effective amount of Ac-TMP-2 protein having at least 95% sequence identity to the amino acid sequence of SEQ ID NO: 2 and that retains anti-inflammatory activity, to thereby reduce or alleviate the inflammation.
2. The method of claim 1, wherein the inflammation is associated with, or secondary to, a disease disorder or condition in the subject.
3. The method of claim 2, wherein the disease, disorder and/or condition is refractory to a baseline therapy.
4. The method of claim 3, wherein the baseline therapy comprises administration of at least one baseline agent selected from the group consisting of nonsteroidal anti-inflammatory drugs (NSAIDs), aminosalicylates, corticosteroids, immunosuppressants, anti-cytokine/cytokine receptor agents, antibiotics, and combinations thereof.
5. The method of claim 3, wherein, at least initially, Ac-TMP-2 protein is administered adjunctively with the baseline therapy.
6. The method of claim 3, wherein, at least initially, Ac-TMP-2 protein is administered adjunctively with the at least one baseline agent, which is administered at less than a full dose.

7. The method of claim 2, wherein the disease, disorder and/or condition is an immunological disease, disorder and/or condition.

8. The method of claim 7, wherein the immunological disease, disorder and/or condition is selected from the group consisting of Addison's disease, ankylosing spondylitis, celiac disease, chronic inflammatory demyelinating polyneuropathy (CIDP), chronic recurrent multifocal ostomyelitis (CRMO), Crohn's disease, demyelinating neuropathies, glomerulonephritis, Goodpasture's syndrome, Graves' disease, Guillain-Barre syndrome, Hashimoto's encephalitis, Hashimoto's thyroiditis, hypogammaglobulinemia, idiopathic thrombocytopenic purpura (ITP), insulin-dependent diabetes (type1), juvenile arthritis, Kawasaki syndrome, multiple sclerosis, myasthenia gravis, postmyocardial infarction syndrome, primary biliary cirrhosis, psoriasis, idiopathic pulmonary fibrosis, Reiter's syndrome, rheumatoid arthritis, sarcoidosis, scleroderma, Sjogren's syndrome, systemic lupus erythematosus (SLE), thrombocytopenic purpura (TTP), ulcerative colitis, vasculitis, vitiligo, and Wegener's granulomatosis.

9. The method of claim 2, wherein the disease is a disease of the digestive tract.

10. The method of claim 9, wherein the disease is chronic gastritis or an inflammatory bowel disease.

11. The method of claim 10, wherein the inflammatory bowel disease is Crohn's disease or ulcerative colitis.

12. The method of claim 8, wherein the disease is a disease of the respiratory system.

13. The method of claim 12, wherein the disease is selected from the group consisting of asthma, emphysema, chronic bronchitis, and chronic obstructive pulmonary disease (COPD).

14. A method for preventing and/or treating an inflammatory bowel disease in a subject, the method including the step of administering to the subject a therapeutically effective amount of Ac-TMP-2 protein having at least 95% identity to the amino acid sequences of SEQ ID NO: 2 and that retains anti-inflammatory activity, to thereby treat the inflammatory bowel disease.

15. The method of claim 14, wherein the inflammatory bowel disease is Crohn's disease or ulcerative colitis.

16. A method for treating asthma in a subject, the method including the step of administering to the subject a therapeutically effective amount of Ac-TMP-2 protein having at least 95% identity to the amino acid sequences of SEQ ID NO: 2 and that retains anti-inflammatory activity, to thereby treat the asthma.

17. The method of any preceding claim, further including the step of administering to the subject at least one additional agent.

18. The method of claim 17, wherein the at least one additional agent is selected from the group consisting of nonsteroidal anti-inflammatory drugs (NSAIDs), aminosalicylates, cortico steroids, immunosuppressants, anti-cytokine/cytokine receptor agents, antibiotics, and combinations thereof.

19. A pharmaceutical composition comprising a therapeutically effective amount of:
 (a) Ac-TMP-2 protein having at least 95% sequence identity to the amino acid sequence of SEQ ID NO: 2 and that retains anti-inflammatory activity, together with a pharmaceutically acceptable carrier, diluent or excipient, and
 (b) at least one additional agent selected from the group consisting of nonsteroidal anti-inflammatory drugs (NSAIDs), aminosalicylates, corticosteroids, immunosuppressants, anti-cytokine/cytokine receptor agents, antibiotics, and combinations thereof.

20. The method of claim 1, wherein the Ac-TMP-2 protein comprises the amino acid sequence of SEQ ID NO: 2.

21. The method of claim 14, wherein the Ac-TMP-2 protein comprises the amino sequence of SEQ ID NO: 2.

22. The method of claim 16, wherein the Ac-TMP-2 protein comprises the amino sequence of SEQ ID NO: 2.

* * * * *

UNITED STATES PATENT AND TRADEMARK OFFICE
CERTIFICATE OF CORRECTION

PATENT NO. : 9,637,527 B2
APPLICATION NO. : 14/384681
DATED : May 2, 2017
INVENTOR(S) : Loukas et al.

It is certified that error appears in the above-identified patent and that said Letters Patent is hereby corrected as shown below:

In the Claims

Column 25, Line 29 Claim 12, "The method of claim 8," should read --The method of claim 2,--.

Signed and Sealed this
Ninth Day of January, 2018

Joseph Matal
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 4

<210> SEQ ID NO 1
<211> LENGTH: 140
<212> TYPE: PRT
<213> ORGANISM: Ancylostoma caninum

<400> SEQUENCE: 1

Met Arg Val Ala Ile Val Phe Ile Ala Cys Phe Ala Val Ala His Ala
1               5                   10                  15

Cys Lys Cys Glu Lys Lys Pro Arg Pro Pro Leu Glu Lys Leu Leu Cys
            20                  25                  30
```

```
Gln Ser Gln Phe Val Thr His Ala Lys Val Thr Lys Lys Arg Ile Asp
        35                  40                  45

Gly Tyr Phe Ile Tyr Tyr Asp Leu Glu His Lys Glu Val Tyr Lys Pro
 50                  55                  60

Lys Asp Arg Ser Ile Pro Ile Glu Leu Phe Ser Trp Arg Glu Lys Glu
 65                  70                  75                  80

Asn Cys Gly Val Pro Asp Leu Glu Glu Gly Lys Glu Tyr Leu Ile Gly
                 85                  90                  95

Gly Lys Val Thr Asp Tyr Gly Asp Gly Asp Leu Val Ile Ser Val Ser
             100                 105                 110

Arg Cys Asp Leu Leu Arg Asn Trp Thr Asp Val Ser Gly Glu Glu Lys
             115                 120                 125

Lys Leu Leu Gly Thr Phe Lys Cys Glu Asn Gln Ser
 130                 135                 140

<210> SEQ ID NO 2
<211> LENGTH: 244
<212> TYPE: PRT
<213> ORGANISM: Ancylostoma caninum

<400> SEQUENCE: 2

Met Ile Ser Leu Ile Val Phe Ile Ala Cys Leu Thr Thr Thr Gln Ala
 1               5                  10                  15

Ala Cys Ser Cys Lys Pro Phe Gly Thr Leu Lys Glu Ala Phe Cys Gln
                 20                  25                  30

Ser Asp Tyr Val Leu Leu Ala Lys Val Leu Ser Val Asn Ser Lys Tyr
             35                  40                  45

Gly Glu Ser Ser Arg Asn Glu Ala Asn Asp Met Ser Thr Thr Ala Asn
 50                  55                  60

Gly Thr Trp Ser Tyr His Val Trp His Met Arg Thr Trp Lys Gly Pro
 65                  70                  75                  80

Val Val Asp Thr Ser Val Leu Thr Thr Ser Tyr Ser Glu Cys Gly Val
                 85                  90                  95

Thr Gly Leu Leu Lys Asn Trp Asp Tyr Phe Leu Thr Gly Lys Gln Gly
             100                 105                 110

Lys Asp Gly Glu Ile Thr Ile Thr Ser Cys Asp Phe Val Met Pro Ser
             115                 120                 125

Thr Asp Val Thr Pro Glu Glu His Asp Leu Leu Met Asp Leu Met Gly
 130                 135                 140

Asp Pro Lys Lys Cys Glu Glu Lys Asp Asp Glu Arg Asp Val Lys Glu
145                 150                 155                 160

Asn Glu Asn Ser Val Glu Glu Asn Asp Glu Lys Asp Glu Glu Asn
                 165                 170                 175

Gly Glu Lys Thr Val Glu Glu Asn Asp Glu Lys Thr Val Glu Glu Asn
             180                 185                 190

Asp Glu Lys Val Glu Glu Asn Gly Glu Lys Thr Val Glu Glu Asn
             195                 200                 205

Asp Glu Lys Thr Val Glu Glu Asn Asp Glu Lys Asp Glu Glu Asn
         210                 215                 220

Gly Glu Lys Thr Val Glu Glu Asn Asp Glu Lys Thr Val Glu Glu Asn
225                 230                 235                 240

Asp Glu Gln Glu
```

<210> SEQ ID NO 3
<211> LENGTH: 519
<212> TYPE: DNA
<213> ORGANISM: Ancylostoma caninum

<400> SEQUENCE: 3

```
agcatatcag catgagagtc gctattgttt tcattgcatg cttcgcagta gcacacgcat     60
gcaagtgcga aagaaacct cgtcctccat tggagaaact gctttgccaa tcacaatttg    120
ttactcacgc gaaagtgacg aagaagagaa ttgatggtta cttcatctat tacgacttgg    180
agcataagga agtttataag cccaaagata ggagtatccc aatcgaactc ttctcatgga    240
gggaaaagga aaattgtggt gttccggatc tcgaagaagg caaagaatac ctgataggag    300
gtaaagtgac ggattatggc gacggtgatt tggtaatttc tgtttcacgg tgcgaccttc    360
tccgaaactg gacagacgtc tctggagagg agaagaaatt gctcggaacg ttcaaatgtg    420
aaaatcagtc ataaacgccg attatatata attgaaagaa gagaaatgaa cattttcac     480 gcgaaaaaaa aaaaaaaaaa aaaaaaaaaa aaaaaaaa                             519
```

<210> SEQ ID NO 4
<211> LENGTH: 870
<212> TYPE: DNA
<213> ORGANISM: Ancylostoma caninum

<400> SEQUENCE: 4

```
cctcgtgccg aatggcacga gggtttgagg tacagaaggg cgccgaagtt atactaaacc     60
catgatttct ctcatagttt tcattgcatg cctcacaacg acgcaggcag catgctcttg    120
caaaccgttc ggaacactga aggaagcttt ctgccaatca gattacgtgc ttctggcaaa    180
agtgttgtca gtaaatagta aatatggtga atcgtcgaga aatgaagcaa atgatatgag    240
cacgaccgct aacggaacat ggagttacca tgtatggcac atgcggactt ggaagggtcc    300
tgtcgttgat actagtgttc tcaccacgtc atatagcgag tgtggtgtaa ctggtctctt    360
gaaaaattgg gattattttc taacaggcaa gcaaggaaaa gatggcgaaa tcaccatcac    420
aagctgcgac tttgtaatgc catcaactga tgtcacacca gaagagcatg atcttttgat    480
ggacctcatg ggggacccga aaaatgtgaa agaaaaagat gatgagaggg acgttaaaga    540
aaacgagaat agcgtagaag agaatgatga gaaagatgaa gaagaaatg gtgagaaaac    600 agtagaagag aatgacgaga aaactgtgga agaaacgat gagaaagttg aagaagaaaa    660
tggtgagaaa acagtagaag agaatgacga gaaactgtg gaagaaacg atgagaaaga    720 tgaagaagaa aatggtgaga aaacagtaga ggagaatgac gagaaaactg tggaagaaaa    780
cgatgaacag gagtgatctg aacactgcaa tttctcgtaa ccaagtggga ataaaattct    840
gacgaaaaaa aaaaaaaaaa aaaaaaaaa                                       870
```